United States Patent
Langer-Anderson et al.

(10) Patent No.: US 11,491,255 B2
(45) Date of Patent: *Nov. 8, 2022

(54) REMOVABLE FILM FORMING GEL COMPOSITIONS AND METHODS FOR THEIR APPLICATION

(71) Applicant: 3M INNOVATIVE PROPERTIES COMPANY, St. Paul, MN (US)

(72) Inventors: Delony L. Langer-Anderson, Hugo, MN (US); George W. Griesgraber, Eagan, MN (US); Semra Colak Atan, St. Louis Park, MN (US); Junia M. Pereira, Woodbury, MN (US); Katie F. Wlaschin, St. Paul, MN (US); Alexi J. Young, Shoreview, MN (US); Robert A. Asmus, Hudson, WI (US); Petra L. Kohler Riedi, Minneapolis, MN (US); David S. Hays, Woodbury, MN (US); Jerald K. Rasmussen, Woodville, WI (US); Michael J. Solberg, Lakeville, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/561,090

(22) PCT Filed: Apr. 4, 2016

(86) PCT No.: PCT/US2016/025904
§ 371 (c)(1),
(2) Date: Sep. 25, 2017

(87) PCT Pub. No.: WO2016/164315
PCT Pub. Date: Oct. 13, 2016

(65) Prior Publication Data
US 2018/0117214 A1    May 3, 2018

Related U.S. Application Data

(60) Provisional application No. 62/240,948, filed on Oct. 13, 2015, provisional application No. 62/143,622, filed on Apr. 6, 2015.

(51) Int. Cl.
| | |
|---|---|
| *A61K 47/34* | (2017.01) |
| *A61K 9/70* | (2006.01) |
| *A61L 26/00* | (2006.01) |
| *A61K 31/14* | (2006.01) |
| *A61L 24/00* | (2006.01) |
| *A61L 24/04* | (2006.01) |

(52) U.S. Cl.
CPC ........ *A61L 26/0066* (2013.01); *A61K 9/7015* (2013.01); *A61K 31/14* (2013.01); *A61K 47/34* (2013.01); *A61L 24/001* (2013.01); *A61L 24/0015* (2013.01); *A61L 24/043* (2013.01); *A61L 26/0004* (2013.01); *A61L 26/0019* (2013.01); *A61L 26/0052* (2013.01); *A61L 26/0061* (2013.01); *A61L 26/0095* (2013.01); *A61L 2300/404* (2013.01); *A61L 2300/418* (2013.01); *A61L 2400/04* (2013.01); *A61L 2430/34* (2013.01); *Y02A 50/30* (2018.01)

(58) Field of Classification Search
None
See application file for complete search history.

(56) References Cited

U.S. PATENT DOCUMENTS

| | | |
|---|---|---|
| 2,676,182 A | 4/1954 | Daudt |
| 3,627,851 A | 12/1971 | Brady |
| 3,772,247 A | 11/1973 | Flannigan |
| 3,928,556 A | 12/1975 | Sweger |
| 4,900,474 A | 2/1990 | Terae |
| 4,935,484 A | 6/1990 | Ruber |
| 4,987,893 A | 1/1991 | Salamone |
| 5,028,679 A | 7/1991 | Terae |
| 5,082,706 A | 1/1992 | Tangney |
| 5,103,812 A | 4/1992 | Salamone |
| 5,118,775 A | 6/1992 | Inomata |
| 5,214,119 A | 5/1993 | Leir |
| 5,236,997 A | 8/1993 | Fujiki |

(Continued)

FOREIGN PATENT DOCUMENTS

| | | |
|---|---|---|
| EP | 1963456 B1 | 9/2011 |
| NZ | 584498 | 10/2010 |

(Continued)

OTHER PUBLICATIONS

Mathur et al., Comparative efficacy of benzalkonium chloride, chloroxylenol and cetrimide-chlorhexidine in humans, Indian Journal of Medical Microbiology. Apr. 1996; 14(2): 77-9, printed from http://medind.nic.in/imvw/imvw11338.html, Abstract only, 1 page.*
Pillai et al., 1,2-Alkanediols for Cosmetic Preservation, Cosmetics & Toiletries; Oct. 28, 2013, printed from https://www.cosmeticsandtoiletries.com/formulating/function/preservatives/premium-12-alkanediols-for-cosmetic-preservation-228198361.html, 1 page, Abstract only.*
Rabea et al., Chitosan as antimicrobial agent: applications and mode of action, Biomacromolecules, Nov.-Dec. 2003;4(6):1457-65, printed from https://pubmed.ncbi.nlm.nih.gov/14606868/, abstract only, 1 page.*

(Continued)

*Primary Examiner* — Gigi G Huang
(74) *Attorney, Agent, or Firm* — Jeffrey M. Olofson

(57) ABSTRACT

Film forming gel compositions, useful in creating conformable and flexible gel bandages, can be formulate from a film-forming polymer, a tackifier, and a volatile solvent. The film forming gels can also include antiseptics, cationic polymer coagulants, fillers, and other additives. The gel compositions form relatively thick films when dried on tissue, and can exhibit enhanced breathability to promote wound healing.

13 Claims, 5 Drawing Sheets

(56) References Cited

U.S. PATENT DOCUMENTS

| | | | |
|---|---|---|---|
| 5,246,694 A * | 9/1993 | Birthwistle | A61K 8/068 |
| | | | 424/70.12 |
| 5,248,739 A | 9/1993 | Schmidt | |
| 5,302,685 A | 4/1994 | Tsumura | |
| 5,319,040 A | 6/1994 | Wengrovius | |
| 5,461,134 A | 10/1995 | Leir | |
| 5,480,935 A | 1/1996 | Greff | |
| 5,512,650 A | 4/1996 | Leir | |
| 5,558,560 A | 9/1996 | Uchida | |
| 5,712,027 A | 1/1998 | Ali | |
| 5,725,882 A | 3/1998 | Kumar | |
| 5,807,957 A | 9/1998 | Samour | |
| 5,981,621 A | 11/1999 | Clark | |
| 6,007,914 A | 12/1999 | Joseph | |
| 6,040,315 A | 3/2000 | Day | |
| 6,051,216 A | 4/2000 | Barr | |
| 6,143,805 A | 11/2000 | Hickey | |
| 6,183,593 B1 | 2/2001 | Narang | |
| 6,383,502 B1 | 5/2002 | Dunshee | |
| 6,512,072 B1 | 1/2003 | Gantner | |
| 6,569,521 B1 | 5/2003 | Sheridan | |
| 6,664,359 B1 | 12/2003 | Kangas | |
| 7,323,162 B2 | 1/2008 | Martin | |
| 7,371,464 B2 | 5/2008 | Sherman | |
| 7,501,184 B2 | 3/2009 | Leir | |
| 7,651,990 B2 | 1/2010 | Asmus | |
| 7,705,101 B2 | 4/2010 | Sherman | |
| 7,795,326 B2 | 9/2010 | Salamone | |
| 7,947,376 B2 | 5/2011 | Sherman | |
| 8,197,803 B2 | 6/2012 | Salamone | |
| 8,198,326 B2 | 6/2012 | Scholz | |
| 8,263,720 B1 | 9/2012 | Salamone | |
| 8,338,491 B2 | 12/2012 | Asmus | |
| 8,431,671 B2 | 4/2013 | Sherman | |
| 8,435,776 B2 | 5/2013 | Rasmussen | |
| 8,552,136 B2 | 10/2013 | Papp | |
| 8,586,668 B2 | 11/2013 | Leir | |
| 8,808,732 B2 | 8/2014 | Dong | |
| 8,940,325 B2 | 1/2015 | Apert | |
| 10,603,405 B2 * | 3/2020 | Langer-Anderson | |
| | | | A61L 26/0052 |
| 2003/0082129 A1 * | 5/2003 | Buckingham | A61K 8/046 |
| | | | 424/70.12 |
| 2005/0131138 A1 | 6/2005 | Connor et al. | |
| 2005/0249791 A1 * | 11/2005 | Hobbs | A61L 15/46 |
| | | | 424/443 |
| 2007/0053859 A1 * | 3/2007 | Bui | A61K 8/31 |
| | | | 424/63 |
| 2007/0129474 A1 | 6/2007 | Salamone | |
| 2007/0148475 A1 * | 6/2007 | Sherman | C09J 177/06 |
| | | | 428/447 |
| 2008/0152614 A1 | 6/2008 | Dunshee | |
| 2009/0000727 A1 | 1/2009 | Kumar | |
| 2009/0004132 A1 | 1/2009 | Nicholson | |
| 2011/0123479 A1 | 5/2011 | Heckroth | |
| 2011/0217752 A1 * | 9/2011 | Rasmussen | C08G 69/10 |
| | | | 435/183 |
| 2012/0021027 A1 * | 1/2012 | Hodgson | A61K 8/0204 |
| | | | 424/401 |
| 2012/0241391 A1 | 9/2012 | Carlson | |
| 2014/0127148 A1 | 5/2014 | Derain | |
| 2014/0127320 A1 | 5/2014 | Salamone | |
| 2014/0130711 A1 | 5/2014 | Derain | |
| 2014/0154188 A1 | 6/2014 | Derain | |
| 2014/0228475 A1 | 8/2014 | Asmus | |
| 2015/0079203 A1 | 3/2015 | Thomas | |

FOREIGN PATENT DOCUMENTS

| | | |
|---|---|---|
| WO | WO 1996-34028 | 10/1996 |
| WO | WO 1996-34030 | 10/1996 |
| WO | WO 1996-35458 | 11/1996 |
| WO | WO 1997-40103 | 10/1997 |
| WO | WO 1998-17726 | 4/1998 |
| WO | WO 2005/120473 | 12/2005 |
| WO | WO 2009-045752 | 4/2009 |
| WO | WO 2011/109151 | 9/2011 |
| WO | WO 2013-156237 | 10/2013 |
| WO | WO 2014-008264 | 1/2014 |
| WO | WO 2014-093093 | 6/2014 |

OTHER PUBLICATIONS

Cheah et al., Chitosan coating for inhibition of sclerotinia rot of carrots, New Zealand Journal of Crop and Horticultural Science, 1997, 25:1, 89-92, printed from https://www.tandfonline.com/doi/abs/10.1080/01140671.1997.9513992, abstract only, 4 pages.*
Encyclopedia of Polymer Science and Engineering, 265-270 (1989).
Katritzky, Comprehensive Organic Functional Group Transformation, 640 (2005).
Rose, "Bisdiguanides having Antibacterial Activity", Journal of the Chemical Society, 1956, pp. 4422-4425.
International Search Report for PCT International Application No. PCT/US2016/25904, dated Jul. 7, 2016, 2pgs.
"Chitosan Bandage for Faster Blood Clotting and Wound Healing", Monica Sanandam et al., [available on the internet Jan. 1, 2013], [retrieved from the internet on Oct. 24, 2018], URL <https://www.researchgate.net/profile/Kiran_Shejale/publication/263244625_CHITOSAN_BANDAGE_FOR_FASTER_BLOOD_CLOTTING_AND_WOUND_HEALING/links/0046353a41cedb3fdf000000/CHITOSAN-BANDAGE-FOR-FASTER-BLOOD-CLOTTING-AND-WOUND-HEALING.pdf >, 5 pp.

* cited by examiner

REMOVABLE FILM FORMING GEL COMPOSITIONS AND METHODS FOR THEIR APPLICATION

RELATED APPLICATIONS

This patent application claims the benefit of and priority to U.S. Provisional Application No. 62/143,622, filed on Apr. 6, 2015, and also claims the benefit of and priority to U.S. Provisional Application No. 62/240,948, filed on Oct. 13, 2015. This application is also related to Attorney Docket No. 77065WO003, entitled "Removable Film Forming Gel Compositions and Methods for Their Application". All of the aforementioned applications are incorporated by reference herein in their entirety.

SUMMARY

The present disclosure provides easy to apply gel compositions that dry to form durable film bandages and other tissues protectants. The film forming, gel compositions of the present disclosure can be flexible, breathable, waterproof, non-stinging, gentle to skin, and easy to remove by peeling or other wearer generated force. The gel compositions, when dried, possess enhanced cohesion and integrity. If desired, the gel compositions are capable of absorbing moisture and wound exudate, particularly blood. Accordingly, the film forming compositions are particularly well suited for use as a liquid bandage or skin protectant. The gel compositions are useful for protecting or treating skin, tissues, organs, nails, hydrated tissues and mucous membranes, e.g., bleeding injuries, surgical site, skin ulcers, cold sores, cuts, rashes, abrasions, incisions and blisters, abraded gums and other oral surfaces, hemorrhoids and abraded body areas, and other mucosal membrane incisions and wounds.

In certain advantageous implementations, neither the gel composition nor the subsequently-formed films irritate the skin and other tissue during application, drying, or during use after drying. The bandages created are desirably substantially painless while worn and can be easily removed by peeling, if desired, substantially without pain or disturbance of the wound site. The dried bandages formed can exhibit high water vapor transmission throughout. The gel composition, when applied over surfaces moist with blood or body fluids, can form a tough, lightly adherent film that can, in certain circumstances, absorb and retain volumes of exudate.

Notably, the gel compositions of the present disclosure can dry to a relatively thick, flexible film with the desirable wound healing properties (e.g., breathable, flexible, non-stinging) in a single application. In particular, it is possible that a gel composition applied at a 50-120 mil coating thickness to skin at room temperature, an adherent film can form having a thickness of at least 2 mils, at least 3 mils, at least 4 mils, at least 5 mils, or at least 6 mils. Once dried on skin, the gel compositions exhibit a 180 degree peel adhesion from human skin of no greater than 900 grams per square inch according to a Skin Adhesion Test and a keratin removal level of no greater than 40% according to a Skin Removal Test. Accordingly, the dried films can be removed by application of force without substantial damage to the underlying skin or wound site.

In one aspect, the gel composition includes a film-forming polymer, a compatible tackifier, an antiseptic, a volatile solvent, and optionally a cationic polymer acting as a coagulant. At least the film forming polymer and the tackifier are typically soluble in the solvent. The gel composition may be silicone-based, in that the film forming material includes a silicone-containing polymer. The film forming polymer may be composed of segmented siloxane copolymers, including silicone polyurea block copolymers and polydiorganosiloxane polyoxamide block copolymers. These polymeric materials are typically non-adhesive materials, often having release properties, and can be formulated with silicate tackifying resins (such as MQ resins). A particularly suitable film forming polymer is a polydiorganosiloxane polyoxamide.

In one aspect, the present disclosure provides a film forming gel composition for use as a conformable bandage. The composition comprises a silicone containing polymer, a tackifier comprising a silicate tackifying resin; a coagulant comprising a cationic polymer; and a volatile solvent, wherein a film cast from the composition is self-supporting on a biological substrate and can be removed from the substrate without substantially compromising the integrity of the film or the substrate.

In another aspect, the present disclosure provides a gel composition comprising (a) 10-25 wt. % film forming polymer; (b) 3-6 wt. % tackifier; (c) 0-0.3 wt. % antiseptic; (d) 0-4 wt. % filler; (e) 60-80 wt. % volatile solvent; (f) 0-6 wt. % cationic polymer, and (g) 0.5-2 wt. % silicone surfactant, based on the total weight of the gel composition.

In yet another aspect, the present disclosure provides a film useful as a conformable bandage, wherein the film exhibits an upright MVTR of at least 300 $g/m^2/24$ hours, a Skin Adhesion of at least 50 g/inch and no greater than 900 g/inch, an elongation of at least 100%, and an ultimate tensile strength of at least 0.3 MPa. At least a portion of the film has a thickness of at least 2 mils and no greater than 20 mils, and the film is self-supporting and consists of a single layer.

The film can include: (a) 50-75 wt. % silicone containing, film forming polymer; (b) 15-30 wt. % tackifier; (c) 0.1-0.5 wt. % antiseptic; (d) 0-12 wt. % filler; (e) 0-25 wt. % cationic polymer, and (f) 1-15 wt. % silicone surfactant, based on the total weight of the film.

The terms "comprises" and variations thereof do not have a limiting meaning where these terms appear in the description and claims.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As recited herein, all numbers should be considered modified by the term "about" unless stated otherwise.

As used herein, "a," "an," "the," "at least one," and "one or more" are used interchangeably. Thus, for example, a composition comprising "a" cationic antimicrobial agent can be interpreted as a gel composition comprising "one or more" cationic antimicrobial agents.

Also herein, the recitations of numerical ranges by endpoints include all numbers subsumed within that range (e.g., 1 to 5 includes 1, 1.5, 2, 2.75, 3, 3.80, 4, 5, etc.).

As used herein as a modifier to a property or attribute, the term "generally", unless otherwise specifically defined, means that the property or attribute would be readily recognizable by a person of ordinary skill but without requiring absolute precision or a perfect match (e.g., within +/−20% for quantifiable properties). The term "substantially", unless otherwise specifically defined, means to a high degree of approximation (e.g., within +/−10% for quantifiable properties) but again without requiring absolute precision or a perfect match. Terms such as same, equal, uniform, constant, strictly, and the like, are understood to be within the usual tolerances or measuring error applicable to the particular circumstance rather than requiring absolute precision or a perfect match.

The term "polydiorganosiloxane" refers to a divalent segment of formula

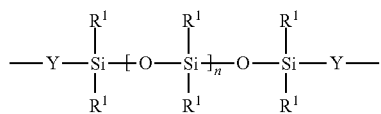

where each $R^1$ is independently an alkyl, haloalkyl, aralkyl, alkenyl, aryl, or aryl substituted with an alkyl, alkoxy, or halo; each Y is independently an alkylene, aralkylene, or a combination thereof; and subscript n is independently an integer of 0 to 1500.

As used herein, "film-forming" refers to a composition when allowed to dry under ambient conditions (e.g., 23° C. and 50% relative humidity (RH)) on skin or mucosal tissue forms a continuous layer that does not flake off after simple flexing of the tissue.

As used herein, "moisture vapor transmission rate" (MVTR), also referred to as "water vapor transmission rate" (WVTR), is a measure of the passage of water vapor through a substance.

As used herein "ready to use" refers to the composition intended to be applied (e.g., to skin or mucosal tissue) without dilution. It should be understood that (unless otherwise specified) the listed amounts of all identified components are for "ready to use" gel compositions.

As used herein, "active kill" means to render a microorganism ineffective by killing (e.g., bacteria and fungi) or otherwise rendering inactive (e.g., viruses) and may be distinguished from disrupting microorganism adhesion or mere bacteriostatic activity. Typically, an active kill results in at least a 0.5 log reduction using the Antimicrobial Efficacy Test described herein, and is desirably at least a 1 log reduction, more preferably at least a 2 log reduction, even more preferably at least a 3 log reduction. It should be understood that in the compositions described herein, the concentrations or amounts of the components, when considered separately, may not kill to an acceptable level, or may not kill as broad a spectrum of undesired microorganisms, or may not kill as fast; however, when used together such components provide an enhanced (preferably synergistic) antimicrobial activity (as compared to the same components used alone under the same conditions).

The above summary of the present disclosure is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exhaustive list.

Figure 1:
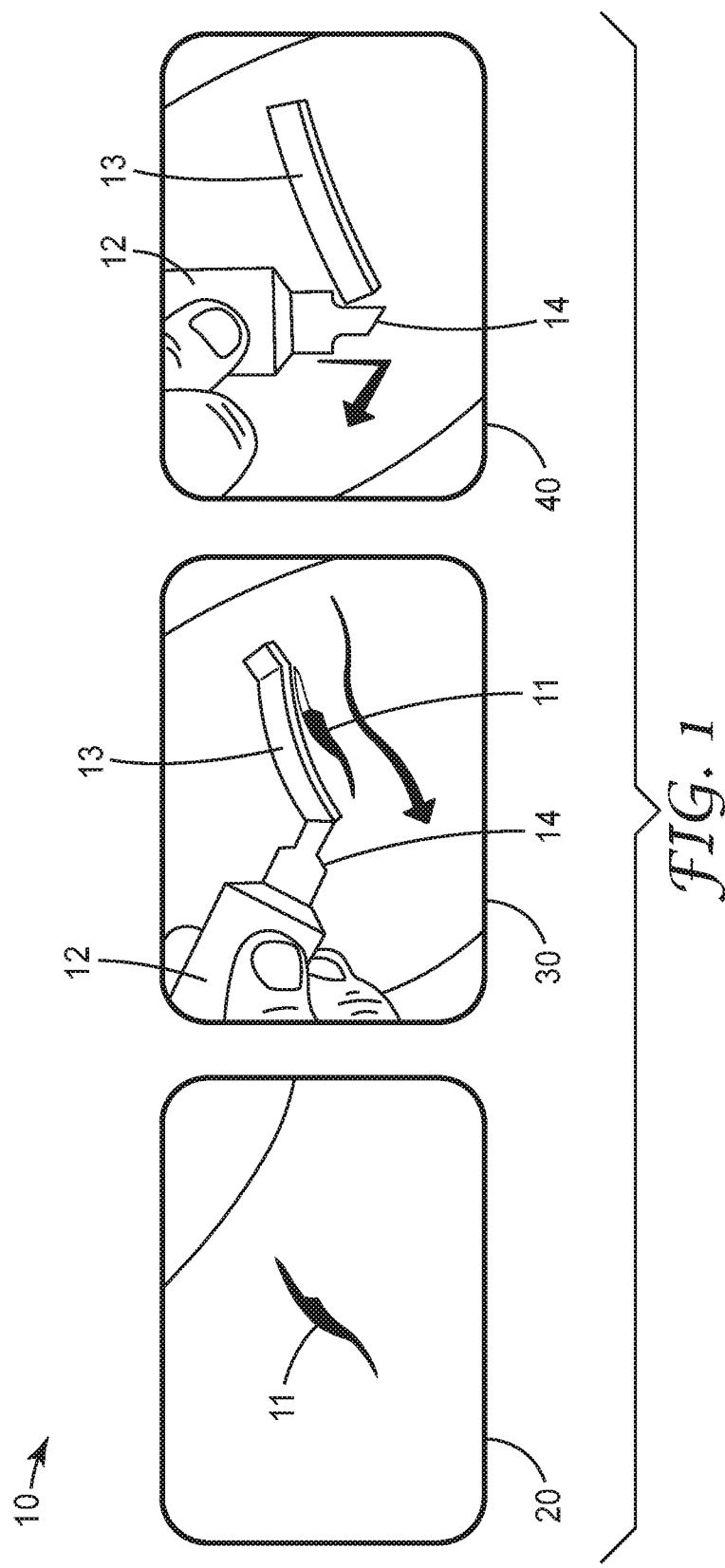
FIG. 1 is a flow chart of a method of applying a gel composition of the present disclosure to a target site.

While the above-identified figures set forth several embodiments of the disclosure other embodiments are also contemplated, as noted in the description. In all cases, this disclosure presents the invention by way of representation and not limitation. It should be understood that numerous other modifications and embodiments can be devised by those skilled in the art, which fall within the scope and spirit of the principles of the invention.

DETAILED DESCRIPTION OF ILLUSTRATIVE EMBODIMENTS

The present disclosure provides myriad flexible, breathable, non-stinging, gentle to skin, self-supporting, and film-forming compositions. The gel composition used in forming a bandage or other protectant typically includes a silicone-containing, film-forming polymer, a tackifier, a coagulant, an antiseptic, and a volatile solvent. Other compositions may exclude antiseptic, coagulant, or both. The gel compositions of the present disclosure may also include fillers, antibiotics, surfactants, and other additives to enhance user comfort or treatment (e.g., release agents to the underlying area of covered tissue). It is a particular feature of the disclosure that the gel materials can act at room temperature (20° C.) when applied to tissues of a user to form films in minutes or less. The films are conformable, comfortable and can be elastic and flexible. The films do not significantly irritate the skin and mucous membrane when deposited during application and in use after drying. The dried films are substantially painless and can be removed substantially without pain. The dried bandages formed are substantially non-water sensitive and have high moisture vapor transmission therethrough. The bandages can form when applied over surfaces wet with water, blood or body fluids, in short times at standard room temperature and reasonable variants thereof. The use of gel compositions over certain bleeding or exudating wounds provides a stark advantage over previously available compositions, which rely on the maintenance of dry or drier target surfaces. The compositions of the present disclosure also tend to be easier to coat in relatively thicker applications, which are more visible to the user and consequently easier to remove. The combination of features allows the compositions of the present disclosure to cover and protect myriad open wounds. Protectable wounds include, but are not limited to, abrasions, lacerations, scrapes, punctures, burns, and pressure sores.

Certain gel compositions of the present disclosure, particularly antiseptic compositions, include one or more of the following characteristics: relatively high levels of bacterial kill if an antimicrobial agent is present (or if the composition is inherently antimicrobial); relatively short dry times; generally clear viewing of the underlying tissue; good adhesion to the skin when dry; little or no tack when dry; capable of releasing an active agent such as an antimicrobial agent or a coagulant; and can be removed relatively easily in a single continuous film, preferably without the need for organic solvent-based removers or other dissolution.

In other implementations, the gel compositions may be used to secure medical articles to the skin or other tissue. Useful medical articles that can be secured by dried films resulting from such gel compositions include, but are not limited to: nasal gastric tubes, blood stream catheters, dialysis catheters and tubing stents, surgical tools, tympanoplasty tubes, shunts including shunts for hydrocephalus, post-surgical drain tubes and drain devices, urinary catheters, endotraecheal tubes, other implantable devices, and other indwelling devices.

Dry times of the film of the present disclosure are preferably no greater than about 5 minutes, more preferably no greater than about 3 minutes, even more preferably no greater than about 2 minutes, and most preferably no greater than about 1.5 minutes on skin measured at 23° C. at 45-55% relative humidity. Dry time can be considered as the minimum time for a composition applied at a defined coat weight to be visibly dry, demonstrate no transfer of the composition to a latex gloved covered hand, and have a minimum level of tack. Dry time of a given composition can be measured under ASTM D 5895-13, particularly with a circular time drying recorder (Test Method B). Dry time measured under this method may be longer than those experienced on skin. Note that the composition may be tack free (in that no composition transfers to a gloved hand) and yet still be not completely dry. Accordingly, tack free times are preferably no greater than about 2 minutes, no greater than about 1 minutes, and in some implementations no greater than about 30 seconds.

The desired specific viscosity of the gel composition depends, in part, on the intended application. For example, where application is to be made to a specific position on the skin (e.g., elbow surfaces, knee surfaces and the like), higher viscosity compositions are preferred to prevent "running" of the compositions to unintended locations. Preferred compositions, in present circumstances, of the present disclosure also possess viscosities that ensure the applied gel easily conforms to tissues while drying, does not run, and forms a relatively thick film. For conformable films the viscosity of a gel composition is at least 20,000 Centipoise (cps), at least 50,000 cps, at least 60,000 cps and in yet other embodiments at least 70,000 cps. To avoid undue difficulty in applying the gel composition to the target area, the viscosity is no greater than about 1,100,000 cps, no greater than about 800,000 cps, no greater than about 600,000 cps, no greater than about 400,000 cps and in yet other implementations no greater than about 250,000 cps when measured at 23° C. using a Brookfield LVT viscometer and the procedure described in the Examples Section. This viscosity range can, in certain circumstances, ensure that the compositions can be applied to the skin in a uniform film that will dry rapidly and maintain structural integrity throughout wear. Furthermore, certain compositions may benefit from higher viscosities as applied, in that (along with other variables) the higher viscosity composition may exhibit less settling (i.e., fewer constituents settling out of an otherwise dissolved or dispersed composition). Applicants have found that certain gel compositions with specific viscosity in the range of 200,000 to 500,000 cps (and particularly 250,000 to 400,000 cps) can be easier to apply, position, and dry while still resulting in a protective covering film exhibiting the characteristics and benefits described below.

The dried films of compositions of the present disclosure are generally flexible and durable, and relatively lightly adherent. That is, they do not crack or flake off as brittle films might do and they remain on skin without needing desquamation for removal. Significantly, the film-forming polymer and compatible tackifier contribute to achieving a delicate balance between low tack, breathability, and flexibility. The composition are accordingly useful on surface areas exposed to high levels of movement, e.g., knuckles, knees, elbows, feet and the like. A film of dried gel composition can have a thickness of at least 1, at least 1.5, 2, 4, 8 mils and typically no greater than 25, 20, 15 mils, and 10 mils. As used herein, the term "mil" refers to 0.001 inch and 1 mil is equal to about 0.0025 centimeters or about 0.025 millimeters or about 25 micrometers. While the gel compositions of the present disclosure can be coated in such a manner as to form a film having a uniform or substantially uniform thickness, variations in, for example, the pressure applied or the applicator used can result in variable thickness throughout the film layer. In presently preferred implementations, the thickness of the film over the target (e.g., wound or skin lesion) is at least 2 mils thick, while areas of the film surrounding the target (e.g., unblemished tissue) may exhibit a relatively thinner film thickness. Certain methods of application, including those described below, can assist in providing a more uniform thickness to normalize dry time and enhance protection.

The conformability and durability properties of the dried films can be determined in part by standard tensile and elongation testing. The elongation of the dried film can range from 50, 75, or 100% to 1400%. In some embodiments, the elongation is at least 100% and no greater than 600%. The ultimate tensile strength is typically at least 0.2, 0.3, or 0.4 MPa and is typically no greater than 2 MPa. In some embodiments, the ultimate tensile strength is no greater than 2, 1.5, or 1 MPa. The Young's elastic modulus is typically at least 0.5, 0.6, 0.7, 0.8, 0.9 or 1 MPa and is typically no greater than about 2 MPa. In some embodiments, the Young's elastic modulus of a tested film is at least 0.7 MPa and typically no greater than 1.5 MPa. Such tensile and elongation properties can be measured, for example, by the methods outlined in ASTM D882-12.

The dried films of compositions of the present disclosure are also relatively lightly adherent. Suitable films typically exhibit a peel adhesion to skin according to the Skin Adhesion Test, described below, of at least 25 g/inch, in some embodiments at least 50 g/inch, and in some embodiments at least 75 g/inch. Suitable dried films typically exhibit a peel adhesion according to the Skin Adhesion Test of no greater than 1000 g/inch, in some embodiments no greater than 900 g/inch, in some embodiments no greater than 600 g/inch. A relatively light adherent film within the above range is typically capable of remaining on the surface to which is applied during desired wear period and is advantageously also capable of being pulled away (e.g., with user applied force) without causing rupture or tearing of the surface: for biological surfaces such as skin, without removing portions of the epidermis or damaging skin, scars or tissue underneath the film. This can be a significant advantage over silicone-containing liquid bandages of the prior art, which often rely on the normal desquamation at the applied site for adequate removal (see e.g., U.S. Pat. No. 8,197,803 (Salamone et al.))

The dried films cast from the gel compositions of the present disclosure can exhibit moisture vapor transmission rates of at least 300 g/m$^2$/24, thus both preventing dehydration of the wounded area and promoting moist wound healing. Herein, dry MVTR (or upright MVTR) of the dried film bandage is measured by ASTM E-96-80 at 40° C. and 20% relative humidity using an upright cup method. Wet MVTR (or inverted MVTR) is measured by the same method except that the sample jars are inverted so the water is in direct contact with the test sample.

Factors influencing the MVTR of a dried film from the inventive gel compositions include, but are not limited to, the thickness of the film layer on the tissue, relative amount of solids in the gel composition before application, the formulation of the gel composition, the viscosity of the gel composition, and the coating structure (i.e., continuous film, or pattern) of the gel. The dried films cast from the gel compositions of the present disclosure exhibit a dry MVTR of at least 300 g/m$^2$/24 hours, more preferably at least 500 g/m$^2$/24 hours, even more preferably at least 1000 g/m$^2$/24 hours, and even more preferably at least 1500 g/m$^2$/24 hours. The dried films preferably have a wet MVTR of at least 500 g/m2/24 hours, more preferably at least 900 g/m2/24 hours, even more preferably at least 1000 g/m2/24 hours, and even more preferably at least 1300 g/m2/24 hours. Different regions of the film may include different dry and/or wet MVTR values.

Surprisingly, the gel compositions exhibit the above, enhanced MVTRs even when applied at the greater coating weight with higher percent solids (and having resultant greater film thickness) than common liquid bandages. Thanks in part to this breathability and other components, the dried films of the present composition can enhance wound healing by increasing the rate of wound reepithelization. The gel compositions of this disclosure may be applied to the skin, mucous membranes, etc. in liquid form by utilization of a brush, rod, finger, sponge, cloth, dropper, etc.; in spray or mist form; or any other usable technique for applying a liquid to a surface such as a wipe, swab or solid paddle applicator. In certain advantageous implementations, the compositions are applied at a wet coat thickness between 25 mils and 150 mils, and in certain implementations between 40 mils and 100 mils. It is typically preferred, after drying, that the resultant films have a thickness of from about 2 to about 20 mils. A relatively thicker film can be advantageous for site protection and ease of removal, but will typically require a longer dry time than relatively thinner films of the same composition. Overall, in one embodiment, the total solids content of the gel composition is at least 15 wt. %, and in one embodiment is at least 20% wt., and in one embodiment is less than 35% wt. of the total gel composition.

Advantageously, the dried films of the present disclosure are self-supporting after a single application of gel composition. As used herein, a "self-supporting" film exhibits the desired combination of breathability, durability, and flexibility in a single strata and without the application of additional layers of gel composition on an outer surface of a dried film. Moreover, a "self-supporting" film does not require an additional, flexible backing for continued wear (i.e., at least 8 hours of continuous existence on the skin or other target tissues). One presently desirable film exhibits an upright MVTR of at least 300 g/m$^2$/24 hours, a film thickness of at least 2 mils and no greater than 20 mils, a skin adhesion of no greater than 900 g/inch, an elongation of at least 100%, and an ultimate tensile strength of at least 0.4 MPa.

Typical gel compositions comprise (a) 10-15 wt. % film forming polymer, (b) 3-5 wt. % tackifier (c) 0-0.3 wt. % antiseptic, (d) 0-3% filler, (e) 60-80 wt. % solvent, (f) 0-5 wt. % cationic polymer, and optionally (g) 0.1-2 wt. % silicone surfactant, based on the total weight of the gel composition.

Dried films of the present disclosure typically comprise (a) 50-75% film forming polymer, (b) 15-30 wt. % tackifier (c) 0.1-0.5 wt. % antiseptic, (d) 0-12 wt. % filler, and (e) 0-20 wt. % cationic polymer and optionally (f) 0.5-15 wt. % silicone surfactant, based on the total weight of the dried film.

Film Forming Polymer

In one aspect, the gel compositions of the present disclosure include a film forming polymer which is capable of forming a substantially continuous layer upon drying. Suitable film forming polymers are at least partially soluble in a volatile solvent, and include silicone-containing polymers. Particularly suitable silicone containing polymers include polysiloxane polyamides, silicone polyureas, and silicone polyamines.

The film forming polymer is typically soluble in the solvent system used in the gel composition. As used herein, a polymer is "soluble" or "solubilized" if the amount of polymer present in the solvent system is completely dissolved in the solvent system without the polymer forming a precipitate or visible, swollen gel particles in solution. As used herein, the term "solubility limit" is the maximum amount, measured as a percentage of the total weight of the solution, of a given polymer that can be dissolved in a given solvent system. For example, the film forming polymer can have a solubility limit of at least 5 wt-%, at least 10 wt-%, at least 15 wt-%, at least 20 wt-%, in the hexamethyldisiloxane (HMDS), isooctane or any other solvent system described herein, based on the total weight of the gel composition.

Silicone-containing polymers useful for practicing the present disclosure may have an intrinsic viscosity ("IV") of at least 0.9, at least 1.45, at least 1.68, or at least 1.8. The silicone containing polymer typically has an intrinsic viscosity less than 3, as polymers having an intrinsic viscosity above 3 can be difficult to solubilize in certain circumstances. Lower IV polymers have notably higher solubility in the solvents and solvent systems and hence, while they can be film formers, they can be slower to dry and remain tacky after application. The IV of the polymers may be controlled by varying initiator, initiator concentration, reaction temperature, reaction solvent, reaction method, and other parameters known to those skilled in the art.

Siloxanes & Polysiloxane Polyamides

Siloxane polymers have unique properties derived mainly from the physical and chemical characteristics of the siloxane bond. These properties include low glass transition temperature, thermal and oxidative stability, resistance to ultraviolet radiation, low surface energy and hydrophobicity. The siloxane polymers, however, often lack tensile strength. The low tensile strength of the siloxane polymers can be improved by forming block copolymers. Some block copolymers contain a "soft" siloxane polymeric block or segment and any of a variety of "hard" blocks or segments. Particularly suitable elastomeric siloxane-based elastomeric polymers are the segmented polymers of Formula 1 and Formula 2 below.

In some embodiments, the silicone-containing polymer is a linear polydiorganosiloxane, a linear polydiorganosiloxane polyamide block copolymer or a polydiorganosiloxane urethane-containing copolymer, but other silicone-containing polymers may be useful.

A polydiorganosiloxane can have a variety of organic substituents on the silicon carbon atoms of the polysiloxane. For example, each organic substituent can be is independently an alkyl, haloalkyl, arylalkylenyl, alkylarylenyl, alkenyl, aryl, or aryl substituted with an alkyl, alkoxy, or halo. The polydiorganosiloxane may have repeating units of the general formula $(Si(R^7)_2O-)$ wherein $R^7$ is as defined below for any of the embodiments of $R^7$ in Formula I. Examples include dimethylsilicones, diethylsilicones, and diphenylsilicones. In some embodiments, at least 40 percent, and in some embodiments at least 50 percent, at least 60 percent, at least 70 percent, at least 80 percent, at least 90 percent, at least 95 percent, at least 98 percent, or at least 99 percent of the $R^7$ groups can be phenyl, methyl, or combinations thereof. In some embodiments, at least 40 percent, at least 50 percent, at least 60 percent, at least 70 percent, at least 80 percent, at least 90 percent, at least 95 percent, at least 98 percent, or at least 99 percent of the $R^7$ groups are methyl. High molecular weight polydimethylsiloxane (PDMS) is commercially available, for example, from Dow Corning Corporation, Midland, Mich.

A linear, polydiorganosiloxane polyamide block copolymer useful for practicing the present disclosure contains at least two repeat units of Formula I:

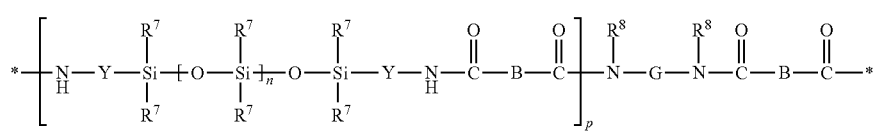

In this formula, each $R^7$ is independently an alkyl, haloalkyl, arylalkylenyl, alkylarylenyl, alkenyl, aryl, or aryl substituted with an alkyl, alkoxy, or halo. Each Y is independently an alkylene, arylalkylene, alkylarylene, or a combination thereof. Subscript n is independently in a range from 0 to 1500 and subscript p is in a range from 1 to 10. Each group B is independently a covalent bond, an alkylene, an arylalkylene, an alkylarylene, an arylene, or a combination thereof. When each group B is a covalent bond, the polydiorganosiloxane polyamide block copolymer of Formula I is referred to as a polydiorganosiloxane polyoxamide block copolymer.

Group G is a divalent group that is the residue unit that is equal to a diamine of formula
$R^8HN$-G-$NHR^8$ minus the two —$NHR^8$ groups. Group $R^8$ is hydrogen or alkyl (e.g., an alkyl having 1 to 10, 1 to 6, or 1 to 4 carbon atoms) or $R^8$ taken together with G and with the nitrogen to which they are both attached forms a heterocyclic group. Each asterisk (*) indicates a site of attachment of the repeat unit to another group in the copolymer such as, for example, another repeat unit of Formula I.

Suitable alkyl groups for $R^7$ in Formula I typically have 1 to 10, 1 to 6, or 1 to 4 carbon atoms. Examples of useful alkyl groups include methyl, ethyl, isopropyl, n-propyl, n-butyl, and iso-butyl. Suitable haloalkyl groups for $R^7$ often have only a portion of the hydrogen atoms of the corresponding alkyl group replaced with a halogen. Examples of haloalkyl groups include chloroalkyl and fluoroalkyl groups with 1 to 3 halo atoms and 3 to 10 carbon atoms. Suitable alkenyl groups for $R^7$ often have 2 to 10 carbon atoms. Examples of alkenyl groups often have 2 to 8, 2 to 6, or 2 to 4 carbon atoms such as ethenyl, n-propenyl, and n-butenyl. Suitable aryl groups for $R^7$ often have 6 to 12 carbon atoms. Phenyl is an example of an aryl group. The aryl group can be unsubstituted or substituted with an alkyl (i.e., it may be an alklyarylenyl group) (the alkyl group may be, e.g., an alkyl having 1 to 10 carbon atoms, 1 to 6 carbon atoms, or 1 to 4 carbon atoms), an alkoxy (e.g., an alkoxy having 1 to 10 carbon atoms, 1 to 6 carbon atoms, or 1 to 4 carbon atoms), or halo (e.g., chloro, bromo, or fluoro). Suitable arylalkylenyl and alkylarylenyl groups for $R^7$ usually have an alkylene group with 1 to 10 carbon atoms and an aryl group with 6 to 12 carbon atoms. In some arylalkylenyl and alkylarylenyl groups, the aryl group is phenyl and the alkylene group has 1 to 10 carbon atoms, 1 to 6 carbon atoms, or 1 to 4 carbon atom. For example, $R^7$ may be an arylalkylenyl group where any of these alkylene groups is bonded to a phenyl group.

In some embodiments, in some repeat units of Formula I, at least 40 percent, and in some embodiments at least 50 percent, of the $R^7$ groups are phenyl, methyl, or combinations thereof. For example, at least 60 percent, at least 70 percent, at least 80 percent, at least 90 percent, at least 95 percent, at least 98 percent, or at least 99 percent of the $R^7$ groups can be phenyl, methyl, or combinations thereof. In some embodiments, in some repeat units of Formula I, at least 40 percent, and in some embodiments at least 50 percent, of the $R^7$ groups are methyl. For example, at least 60 percent, at least 70 percent, at least 80 percent, at least 90 percent, at least 95 percent, at least 98 percent, or at least 99 percent of the $R^7$ groups can be methyl. The remaining $R^7$ groups can be selected from an alkyl having at least two carbon atoms, haloalkyl, arylalkylenyl, alkylarylenyl, alkenyl, aryl, or aryl substituted with an alkyl, alkoxy, or halo.

Each Y in Formula I is independently an alkylene, arylalkylene, alkylarylene, or a combination thereof. Suitable alkylene groups typically have up to 10 carbon atoms, up to 8 carbon atoms, up to 6 carbon atoms, or up to 4 carbon atoms. Examples of alkylene groups include methylene, ethylene, propylene, butylene, and the like. Suitable arylalkylene and alkylarylene groups usually have an arylene group with 6 to 12 carbon atoms bonded to an alkylene group with 1 to 10 carbon atoms. In some arylalkylene and alkylarylene groups, the arylene portion is phenylene. That is, the divalent arylalkylene or alkylarylene group has phenylene bonded to an alkylene having 1 to 10, 1 to 8, 1 to 6, or 1 to 4 carbon atoms. As used herein with reference to group Y, "a combination thereof" refers to a combination of two or more groups selected from an alkylene and arylalkylene or alkylarylene group. A combination can be, for example, a single alkylarylene bonded to a single alkylene (e.g., alkylene-arylene-alkylene). In one example of an alkylene-arylene-alkylene combination, the arylene is phenylene and each alkylene has 1 to 10, 1 to 6, or 1 to 4 carbon atoms.

Each subscript n in Formula I is independently in a range from 0 to 1500. For example, subscript n can be up to 1000, up to 500, up to 400, up to 300, up to 200, up to 100, up to 80, up to 60, up to 40, up to 20, or up to 10. The value of n is often at least 1, at least 2, at least 3, at least 5, at least 10, at least 20, or at least 40. For example, subscript n can be in the range of 40 to 1500, 0 to 1000, 40 to 1000, 0 to 500, 1 to 500, 40 to 500, 1 to 400, 1 to 300, 1 to 200, 1 to 100, 1 to 80, 1 to 40, or 1 to 20.

The subscript p is in a range from 1 to 10. For example, the value of p is often an integer up to 9, up to 8, up to 7, up to 6, up to 5, up to 4, up to 3, or up to 2. The value of p can be in the range of 1 to 8, 1 to 6, or 1 to 4.

Group G in Formula I is a residual unit that is equal to a diamine compound of formula $R^8$HN-G-NH$R^8$ minus the two amino groups (i.e., —NH$R^8$ groups). The diamine can have primary or secondary amino groups. Group $R^8$ is hydrogen or alkyl (e.g., an alkyl having 1 to 10, 1 to 6, or 1 to 4 carbon atoms) or $R^8$ taken together with G and with the nitrogen to which they are both attached forms a heterocyclic group (e.g., a 5- to 7-membered ring). In some embodiments, $R^8$HN-G-NH$R^8$ is piperazine. In some embodiments, $R^8$ is hydrogen or an alkyl. In some embodiments, both of the amino groups of the diamine are primary amino groups (i.e., both $R^8$ groups are hydrogen) and the diamine is represented by formula $H_2$N-G-N$H_2$.

In some embodiments, G is an alkylene, heteroalkylene, polydiorganosiloxane, arylene, arylalkylene, alkylarylene, or a combination thereof. Suitable alkylenes often have 2 to 10, 2 to 6, or 2 to 4 carbon atoms. Examples of alkylene groups include ethylene, propylene, and butylene. Suitable heteroalkylenes are often polyoxyalkylenes such as polyoxyethylene having at least 2 ethylene units, polyoxypropylene having at least 2 propylene units, or copolymers thereof. Examples of polydiorganosiloxanes include polydimethylsiloxanes with alkylene terminal groups. Suitable arylalkylene groups usually contain an arylene group having 6 to 12 carbon atoms bonded to an alkylene group having 1 to 10 carbon atoms. Some examples of arylalkylene groups are phenylene-alkylene where the phenylene is bonded to an alkylene having 1 to 10 carbon atoms, 1 to 8 carbon atoms, 1 to 6 carbon atoms, or 1 to 4 carbon atoms. Some examples of alkylarylene groups are alkylene-phenylene where the alkylene having 1 to 10 carbon atoms, 1 to 8 carbon atoms, 1 to 6 carbon atoms, or 1 to 4 carbon atoms is bonded to a phenylene. As used herein with reference to group G, "a combination thereof" refers to a combination of two or more groups selected from an alkylene, heteroalkylene, polydiorganosiloxane, arylene, arylalkylene, and alkylarylene. A combination can be, for example, an arylalkylene bonded to an alkylene (e.g., alkylene-arylene-alkylene). In one example of an alkylene-arylene-alkylene combination, the arylene is phenylene and each alkylene has 1 to 10, 1 to 6, or 1 to 4 carbon atoms.

In some embodiments, the polydiorganosiloxane polyamide is a polydiorganosiloxane polyoxamide. The polydiorganosiloxane polyoxamide tends to be free of groups having a formula —B—(CO)—NH— where B is an alkylene. All of the carbonylamino groups along the backbone of the copolymeric material typically are part of an oxalylamino group (i.e., the —(CO)—(CO)—NH— group), and B is a bond. That is, any carbonyl group along the backbone of the copolymeric material is bonded to another carbonyl group and is part of an oxalyl group. More specifically, the polydiorganosiloxane polyoxamide has a plurality of aminoxalylamino groups.

The polydiorganosiloxane polyamide is a block copolymer and can be an elastomeric material. Unlike many of the known polydiorganosiloxane polyamides that are generally formulated as brittle solids or hard plastics, the polydiorganosiloxane polyamides can be formulated to include greater than 50 weight percent polydiorganosiloxane segments based on the weight of the copolymer. The weight percent of the diorganosiloxane in the polydiorganosiloxane polyamides can be increased by using higher molecular weight polydiorganosiloxanes segments to provide greater than 60 weight percent, greater than 70 weight percent, greater than 80 weight percent, greater than 90 weight percent, greater than 95 weight percent, or greater than 98 weight percent of the polydiorganosiloxane segments in the polydiorganosiloxane polyamides. Higher amounts of the polydiorganosiloxane can be used to prepare elastomeric materials with lower modulus while maintaining reasonable strength.

Some of the polydiorganosiloxane polyamides can be heated to a temperature up to 200° C., up to 225° C., up to 250° C., up to 275° C., or up to 300° C. without noticeable degradation of the material. For example, when heated in a thermogravimetric analyzer in the presence of air, the copolymers often have less than a 10 percent weight loss when scanned at a rate 50° C. per minute in the range of 20° C. to 350° C. Additionally, the copolymers can often be heated at a temperature such as 250° C. for 1 hour in air without apparent degradation as determined by no detectable loss of mechanical strength upon cooling. The linear block copolymers having repeat units of Formula I can be prepared, for example by reaction of at least one polydiorganosiloxane-containing precursor with at least one diamine as described in U.S. Pat. No. 7,371,464; incorporated herein by reference.

The diamines are sometimes classified as organic diamines or polydiorganosiloxane diamines with the organic diamines including, for example, those selected from alkylene diamines, heteroalkylene diamines (such as polyoxyalkylene diamines), arylene diamines, aralkylene diamines, or alkylene-aralkylene diamines. The diamine has only two amino groups so that the resulting polydiorganosiloxane polyoxamides are linear block copolymers that are often elastomeric, hot melt processable (e.g., the copolymers can be processed at elevated temperatures such as up to 250° C. or higher without apparent degradation of the composition), and soluble in some common organic solvents. The some embodiments, the diamine is free of a polyamine having more than two primary or secondary amino groups. Tertiary amines that do not react with the polydiorganosiloxane-containing precursor of can also be present. Additionally, the diamines utilized in the reaction are free of any carbonylamino group. That is, the diamine is not an amide.

Preferred alkylene diamines (i.e., G is a alkylene) include, but are not limited to, ethylene diamine, propylene diamine, butylene diamine, hexamethylene diamine, 2-methylpentamethylene 1,5-diamine (i.e., commercially available from DuPont, Wilmington, Del. under the trade designation DYTEK A), 1,3-pentane diamine (commercially available from DuPont under the trade designation DYTEK EP), 1,4-cyclohexane diamine, 1,2-cyclohexane diamine (commercially available from DuPont under the trade designation DHC-99), 4,4'-bis(aminocyclohexyl)methane, and 3-aminomethyl-3,5,5-trimethylcyclohexylamine.

The polydiorganosiloxane polyoxamide copolymer can be produced using a plurality of polydiorganosiloxane precursors, a plurality of diamines, or a combination thereof. A plurality of precursors having different average molecular weights can be combined under reaction conditions with a single diamine or with multiple diamines. For example, the precursor of may include a mixture of materials with different values of n, different values of p, or different values of both n and p. The multiple diamines can include, for example, a first diamine that is an organic diamine and a second diamine that is a polydiorganosiloxane diamine. Likewise, a single precursor can be combined under reaction conditions with multiple diamines.

Any suitable reactor or process can be used to prepare the polydiorganosiloxane polyamide copolymer material. The reaction can be conducted using a batch process, semi-batch process, or a continuous process. Exemplary batch processes can be conducted in a reaction vessel equipped with a mechanical stirrer such as a Brabender mixer, provided the product of the reaction is in a molten state has a sufficiently low viscosity to be drained from the reactor. Exemplary semi-batch process can be conducted in a continuously stirred tube, tank, or fluidized bed. Exemplary continuous processes can be conducted in a single screw or twin screw extruder such as a wiped surface counter-rotating or co-rotating twin screw extruder.

The polydiorganosiloxane-containing precursor can be prepared by any known method. In some embodiments, this precursor is prepared according to the following reaction scheme, as described in previously cited U.S. Pat. No. 7,371,464 (Sherman et al.).

positions and methods according to the present disclosure include block copolymers comprising silicone blocks and second blocks derived from a multifunctional isocyanate. At points herein the term silicone-polyurea may be used interchangeable with silicone-polyurethane. Useful silicone polyurea block copolymers are disclosed in, e.g., U.S. Pat. Nos. 5,512,650, 5,214,119, and 5,461,134, and 6,569,521, 6,664,359 (Melancon et al.) as well as International Publication Nos. WO 96/35458, WO 98/17726, WO 96/34028, WO 96/34030 and WO 97/40103.

Blocks derived from an isocyanate may have two functional groups (e.g., —NHCONH— or —NHC(O)O—) attached to a divalent organic radical (such as alkyl groups, cycloalkyl groups, and aryl groups, containing from 1 to 30 carbon atoms). Examples of useful diisocyanate compounds from which second blocks may be derived are ethylene diisocyanate, 1,6-hexylene diisocyanate, 1,12-dodecylene diisocyanate, 4,4'-diphenylmethane diisocyanate, 3,3'-dimethoxy-4,4'-diphenylmethane diisocyanate, 3,3'-dimethyl-4,4'-diphenylmethane diisocyanate, 4,4'-diphenyl diisocyanate, toluene-2,6,-diisocyanate, mixtures of toluene-2,6-diisocyanate and toluene-2,4-diisocyanate, 1,4-cyclohexylene diisocyanate, 4,4'-dicyclohexylmethane diisocyanate, 3,3'-diphenyl-4,4'-biphenylene diisocyanate, 4,4'-biphenylene diisocyanate, 2,4-diisocyanatodiphenylether, 2,4-dimethyl-1,3-phenylene diisocyanate, 4,4'-diphenylether diisocyanate, isophorone diisocyanate, and mixtures thereof.

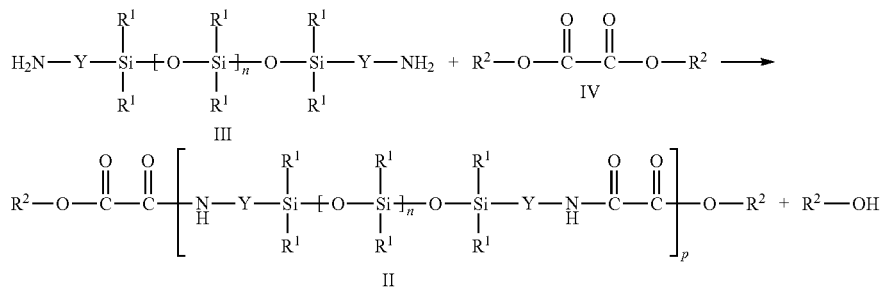

The polydiorganosiloxane diamine can be prepared by any known method and can have any suitable molecular weight.

Further details on suitable polydiorganosiloxane polyamides (including polydiorganosiloxane diamines and particularly polydiorganosiloxane polyoxamide) may be found, for example, among U.S. Pat. No. 8,586,668 (Leir et al), U.S. Pat. No. 5,214,119 (Leir et al.), U.S. Pat. No. 5,461,134 (Leir et al.), U.S. Pat. No. 5,512,650 (Leir et al.), and U.S. Pat. No. 7,371,464 (Sherman et al.), as well as U.S. Pat. Nos. 7,705,101 and 8,431,671 (Sherman et al.). Some polydiorganosiloxane diamines are commercially available, for example, from Shin Etsu Silicones of America, Inc., Torrance, Calif. and from Gelest Inc., Morrisville, Pa.

Other examples of suitable silicone elastomers include polydiorganosiloxane polyuria. copolymers and blends thereof, such as those described in U.S. Pat. Nos. 5,461,134 and 6,007,914 (Joseph et al.). Silicone-polyurethane copolymers (SPU) useful as film forming polymers in the com- Silicone blocks include those having the general formula $(Si(R^7)_2O—)$ wherein $R^7$ is as defined above for any of the embodiments of $R^7$ in Formula I. Non-limiting examples include dimethylsilicones, diethylsilicones, and diphenylsilicones.

Polydiorganosiloxane urethane-containing copolymers (a subset of the class of SPU materials) useful in compositions of the present disclosure contain soft polydiorganosiloxane units, hard polyisocyanate residue units, terminal groups and optionally soft and/or hard organic polyamine residue units. Some polydiorganosiloxane urea-containing copolymers are commercially available under the trade designation "GENIOMER 140" available from Wacker Chemie AG, Germany. The polyisocyanate residue is the polyisocyanate minus the —NCO groups, the organic polyamine residue is the organic polyamine minus the —NH groups, and the polyisocyanate residue is connected to the polydiorganosiloxane units or organic polyamine residues by urea linkages. The terminal groups may be non-functional groups or functional groups depending on the purpose of the polydiorganosiloxane urea segmented copolymer.

In some embodiments, the polydiorganosiloxane urethane containing copolymers useful as polymer processing additives contain at least two repeat units of Formula II

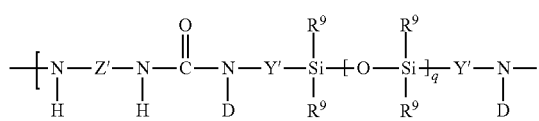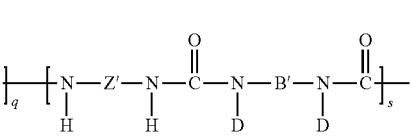

II

In this Formula II each $R^9$ is a moiety that independently is an alkyl, cycloalkyl, aryl, perfluoroalkyl, or a perfluoroether group. In some embodiments of $R^9$, alkyl has about 1 to 12 carbon atoms and may be substituted with, for example, trifluoroalkyl, vinyl, a vinyl radical or higher alkenyl represented by the formula —$R^{10}$ $(CH_2)_a CH$=$CH_2$ wherein $R^{10}$ is —$(CH_2)_b$— or —$(CH_2)_c CH$=$CH$— and a is 1, 2 or 3; b is 0, 3 or 6; and c is 3, 4 or 5. In some embodiments of $R^9$, cycloalkyl has about 6 to 12 carbon atoms and may be substituted with one or more alkyl, fluoroalkyl, or vinyl groups. In some embodiments of $R^9$, aryl has about 6 to 20 carbon atoms and may be substituted with, for example, alkyl, cycloalkyl, fluoroalkyl and vinyl groups. In some embodiments of $R^9$, the perfluoroalkyl group is as described in U.S. Pat. No. 5,028,679, wherein such description is incorporated herein by reference, and the perfluoroether-containing group is as described in U.S. Pat. Nos. 4,900,474 and 5,118,775, wherein such descriptions are incorporated herein by reference. In some embodiments, $R^9$ is a fluorine-containing group is as described in U.S. Pat. No. 5,236,997, wherein such description is incorporated herein by reference. In some embodiments, at least 50% of the $R^9$ moieties are methyl radicals with the balance being monovalent alkyl or substituted alkyl radicals having 1 to 12 carbon atoms, alkenylene radicals, phenyl radicals, or substituted phenyl radicals. In Formula II, each Z' is arylene, arylalkylene, alkylene, or cycloalkylene. In some embodiments of Z', the arylene or arylalkylene has from about 6 to 20 carbon atoms. In some embodiments of Z', alkylene or cycloalkylene radical has from about 6 to 20 carbon atoms. In some embodiments, Z' is 2,6-tolylene, 4,4'-methylenediphenylene, 3,3'-dimethoxy-4,4'-biphenylene, tetramethyl-m-xylylene, 4,4'-methylenedicyclohexylene, 3,5,5-trimethyl-3-methylenecyclohexylene, 1,6-hexamethylene, 1,4-cyclohexylene, 2,2,4-trimethylhexylene, or mixtures thereof. In Formula II, each Y' is independently alkylene, arylalkylene, alkylarylene, or arylene. In some embodiments of Y', alkylene has from 1 to 10 carbon atoms. In some embodiments of Y', the arylalkylene, alkylarylene, or arylene has from 6 to 20 carbon atoms. In Formula II, each D is independently hydrogen, an alkyl radical having 1 to 10 carbon atoms, phenyl, or a radical that completes a ring structure including B' or Y' to form a heterocycle. In Formula II, B is a polyvalent radical selected from the group consisting of alkylene, arylalkylene, alkylarylene, cycloalkylene, phenylene, polyalkylene oxide (e.g., polyethylene oxide, polypropylene oxide, polytetramethylene oxide, and copolymers and mixtures thereof). In Formula II, "s" is a number that is 0 to about 1000; "r" is a number that is equal to or greater than 1; and "q" is a number that is about 5 or larger, in some embodiments about 15 to 2000, and in some embodiments about 30 to 1500.

In the use of polyisocyanates (Z' is a radical having a functionality greater than 2) and polyamines (B' is a radical having a functionality greater than 2), the structure of Formula II will be modified to reflect branching at the polymer backbone. In the use of endcapping agents, the structure of Formula II will be modified to reflect termination of the polydiorganosiloxane urea chain.

The linear block copolymers having repeat units of Formula I and polymdiorganolsiloxane urea containing polymers of Formula II can be prepared, for example, as discussed in U.S. Pat. No. 8,552,136 (Papp et al.).

Other examples of silicone containing polymers include those formed from silanols, silicone hydrides, siloxanes, epoxides, and (meth)acrylates. When the film forming polymer is prepared from (meth)acrylate-functional siloxanes, the polymer is sometimes referred to as a siloxane (meth) acrylate. Additionally, other amphiphilic siloxy-containing polymers have been reported as useful in gel compositions (U.S. Pat. No. 7,795,326 (Salamone et al.)), wherein the hydrophobic siloxysilane monomer is copolymerized with a hydrophilic nitrogen-containing monomer. Other siloxy-containing polymers include block copolymers of polydimethylsiloxane and polyurethane, and block copolymers of polydimethylsiloxane and poly(ethylene glycol). Still, other potentially viable film forming polymers include block copolymers of polystyrene and ethylene/butylene, block copolymers of polystyrene and polyisobutylene, block copolymers of polystyrene and polyisoprene, block copolymers of polystyrene and polybutadiene, block copolymers of polydimethylsiloxane and polyurethanes, polymers of C4-C18 acrylates and methacrylates, butyl rubber, polyisobutylene, and combinations thereof.

Another suitable siloxy-containing monomer for certain gel compositions is based upon the siloxy monomer, 3-methacryloyloxypropyltris(trimethylsiloxy)silane (TRIS). TRIS can be used in combination with both hydrophilic comonomers, such as N-isopropylacrylamide (NIPAM), or hydrophobic comonomers, such as methyl methacrylate, such that the resulting copolymers are soluble in a volatile solvent.

The film forming polymer is typically present in quantities of at least 10 wt. % and no greater than 30 wt. %, based on the total weight of the gel composition, or any amount within that range. In certain implementations, it may be preferred that the film forming polymer is present at a concentration of at least 12 wt. % and no greater than 25 wt. %, based on the total weight of the gel composition.

A dried film cast form the gel composition may include an amount of film forming polymer in a range from 50 wt. % to 70 or 75 wt. % relative to a total weight of the dried film, or any amount within that range.

Alternatively, gel compositions may feature polymerizable cyanoacrylate monomers as the primary film-forming polymer. Cyanoacrylate monomers that may be used include readily polymerizable alpha-cyanoacrylates, including alkyl cyanoacrylates, aryl cyanoacrylates, alkoxyalkyl cyanoacrylates, such as butyl cyanoacrylate and n-butyl cyanoacrylate in particular, octyl cyanoacrylate and 2-octyl cyanoacrylate in particular, ethyl cyanoacrylate, methyl cyanoacrylate, n-dodecyl cyanoacrylate, phenyl 2-cyanoacrylate, methoxyethyl 2-cyanoacrylate, and the like. The composition may be composed of one or more polymerizable cyanoacrylate monomers. Film-forming cyanoacrylates are as discussed in U.S. Pat. No. 6,183,593 (Narang et al.) and U.S. Pat. No. 6,143,805 (Hickey et al.). Polymerizable cyanoacrylate esters in particular are described in U.S. Publication No. 2008/0152614 (Dunshee). Further cyanoacrylate compositions are also disclosed by U.S. Pat. No. 5,480,935 (Greff et al.).

Tackifier

Tackifiers, such as silicate tackifying resins can be added to the film forming polymer to provide or enhance the adhesive properties of the composition. The silicate tackifying resin can influence the physical properties of the resulting gel composition. For example, as silicate tackifying resin content is increased, the glassy to rubbery transition of the gel composition occurs at increasingly higher temperatures. In some exemplary gel compositions, a plurality of silicate tackifying resins can be used to achieve desired performance. Suitable silicate tackifying resins include those resins composed of the following structural units M (i.e., monovalent $R'_3SiO_{1/2}$ units), D (i.e., divalent $R'_2SiO_{2/2}$ units), T (i.e., trivalent $R'SiO_{3/2}$ units), and Q (i.e., quaternary $SiO_{4/2}$ units), and combinations thereof. Typical exemplary silicate resins include MQ silicate tackifying resins, MQD silicate tackifying resins, and MQT silicate tackifying resins. These silicate tackifying resins usually have a number average molecular weight in the range of 100 to 50,000 or in the range of 500 to 15,000 and generally have methyl R' groups.

Such resins are described in, for example, Encyclopedia of Polymer Science and Engineering, vol. 15, John Wiley & Sons, New York, (1989), pp. 265-270, and U.S. Pat. No. 2,676,182 (Daudt et al.), U.S. Pat. No. 3,627,851 (Brady), U.S. Pat. No. 3,772,247 (Flannigan), and U.S. Pat. No. 5,248,739 (Schmidt et al.). Other examples are disclosed in U.S. Pat. No. 5,082,706 (Tangney). The above-described resins are generally prepared in solvent. Dried or solventless, M silicone tackifying resins can be prepared, as described in U.S. Pat. No. 5,319,040 (Wengrovius et al.), U.S. Pat. No. 5,302,685 (Tsumura et al.), and U.S. Pat. No. 4,935,484 (Wolfgruber et al.).

MQ silicate tackifying resins are particularly suitable for several gel compositions of the present disclosure. MQ silicate tackifying resins are copolymeric resins having $R'_3SiO_{1/2}$ units ("M" units) and $SiO_{4/2}$ units ("Q" units), where the M units are bonded to the Q units, each of which is bonded to at least one other Q unit. Some of the $SiO_{4/2}$ units ("Q" units) are bonded to hydroxyl radicals resulting in $HOSiO_{3/2}$ units ("$T^{OH}$" units), thereby accounting for the silicon-bonded hydroxyl content of the silicate tackifying resin, and some are bonded only to other $SiO_{4/2}$ units.

Certain MQ silicate tackifying resins can be prepared by the silica hydrosol capping process described in U.S. Pat. No. 2,676,182 (Daudt et al.) as modified according to U.S. Pat. No. 3,627,851 (Brady), and U.S. Pat. No. 3,772,247 (Flannigan). These modified processes often include limiting the concentration of the sodium silicate solution, and/or the silicon-to-sodium ratio in the sodium silicate, and/or the time before capping the neutralized sodium silicate solution to generally lower values than those disclosed by Daudt et al. The neutralized silica hydrosol is often stabilized with an alcohol, such as 2-propanol, and capped with $R_3SiO_{1/2}$ siloxane units as soon as possible after being neutralized. The level of silicon bonded hydroxyl groups (i.e., silanol) on the MQ resin may be reduced to no greater than 1.5 weight percent, no greater than 1.2 weight percent, no greater than 1.0 weight percent, or no greater than 0.8 weight percent based on the weight of the silicate tackifying resin. This may be accomplished, for example, by reacting hexamethyldisilazane with the silicate tackifying resin. Such a reaction may be catalyzed, for example, with trifluoroacetic acid. Alternatively, trimethylchlorosilane or trimethylsilylacetamide may be reacted with the silicate tackifying resin, a catalyst not being necessary in this case.

The tackifier is typically added to the composition to at least 2 wt. %, in some embodiments at least 3 wt. %, in some embodiments at least 4 wt. %, in some embodiments at least 5 wt. %, based on the total weight of the gel composition. The tackifier is typically present in composition at no greater than 20 wt. %, more preferably no greater than 15 wt. %, and most preferably no greater than 10 wt. % based on the total weight of the composition.

A dried film cast form the gel composition may include an amount of tackifier in a range from 5 wt. % to 25 or 30 wt. % relative to a total weight of the dried film, or any amount within that range. In certain implementations, films featuring less than 16 wt. % tackifier exhibit less adhesion to skin or other tissue than may be desired.

Coagulant

In certain advantageous embodiments, the gel composition includes a cationic polymer that acts as a coagulant and repository for a certain volume of exudate. This cationic polymer typically comprises a crosslinked, guanidinyl-containing polymer. The base polymer in the guanidinyl-containing polymer typically comprises a polyamine polymer; i.e., a polymer having primary or secondary amino groups that may be pendent or catenary, i.e., in the polymer chain. The aminopolymers contain primary or secondary amine groups and can be prepared by chain growth or step growth polymerization procedures with the corresponding monomers. These monomers can also, if desired, be copolymerized with other monomers. The polymer can also be a synthesized or naturally occurring biopolymer. If any of these polymers, irrespective of source, do not contain primary or secondary amine groups, these functional groups can be added by the appropriate graft chemistry.

Useful aminopolymers are water soluble or water-dispersible. As used herein, the term "water soluble" refers to a material that can be dissolved in water. The solubility is typically at least about 0.1 gram per milliliter of water. As used herein, the term "water dispersible" refers to a material that is not water soluble but that can be emulsified or suspended in water.

Examples of amino polymers suitable for use, which are prepared by chain growth polymerization include, but are not limited to: polyvinylamine, poly(N-methylvinylamine), polyallylamine, polyallylmethylamine, polydiallylamine, poly(4-aminomethylstyrene), poly(4-aminostyrene), poly (acrylamide-co-methylaminopropylacrylamide), and poly (acrylamide-co-aminoethylmethacrylate).

Examples of amino polymers suitable for use, which are prepared by step growth polymerization include, but are not limited to: polyethylenimine, polypropylenimine, polylysine, polyaminoamides, polydimethylamine-epichlorohydrin-ethylenediamine, and any of a number of polyaminosiloxanes, which can be built from monomers such as aminopropyltriethoxysilane, N-(2-aminoethyl)-3-aminopropyltrimethoxysilane, N-trimethoxysilylpropyl-N-methylamine, and bis(trimethoxysilylpropyl)amine.

Useful aminopolymers that have primary or secondary amino end groups include, but are not limited to, those formed from polyamidoamine (PAMAM) and polypropylenimine: e.g., DAB-Am and PAMAM dendrimers (or hyperbranched polymers containing the amine or quaternary nitrogen functional group). Exemplary dendrimeric materials formed from PAMAM are commercially available under the trade designation Starburst (PAMAM) dendrimer" (e.g., Generation 0 with 4 primary amino groups, Generation 1 with 8 primary amino groups, Generation 2 with 16 primary amino groups, Generation 3 with 32 primary amino groups, and Generation 4 with 64 primary amino groups) from Aldrich Chemical, Milwaukee, Wis. Dendrimeric materials formed from polypropylenimine is commercially available under the trade designation "DAB-AM" from Aldrich Chemical. For example, DAB-Am-4 is a generation 1 polypropylenimine tetraamine dendrimer with 4 primary amino groups, DAB-Am-8 is a generation 2 polypropylenimine octaamine dendrimer with 8 primary amino groups, DAB-Am-16 is a generation 3 polypropylenimine hexadecaamine with 16 primary amino groups, DAB-Am-32 is a generation 4 polypropylenimine dotriacontaamine dendrimer with 32 primary amino groups, and DAB-Am-64 is a generation 5 polypropylenimine tetrahexacontaamine dendrimer with 64 primary amino groups.

Examples of aminopolymers suitable for use, which are biopolymers include chitosan, and starch, where the latter is grafted with reagents such as methylaminoethylchloride.

Other categories of aminopolymers suitable for use include polyacrylamide homo- or copolymers with amino monomers including aminoalkyl(meth)acrylate, (meth)acrylamidoalkylamine, and diallylamine. Presently preferred aminopolymers include polyaminoamides, polyethylenimine, polyvinylamine, polyallylamine, and polydiallylamine.

Suitable commercially available aminopolymers include, but are not limited to, polyamidoamines such as ANQUAMINE™360, 401, 419, 456, and 701 (Air Products and Chemicals, Allentown, Pa.); LUPASOL™ polyethylenimine polymers such as FG, PR 8515, Waterfree, P, PS (BASF Corporation, Resselaer, N.Y.); polyethylenimine polymers such as CORCAT™ P-600 (EIT Company, Lake Wylie, S.C.); polyoxyalkyleneamines such as JEFFAMINE.™ D-230, D-400, D-2000, HK-511 (XTJ-511), XTJ-510 (D-4000), XTJ-500 (ED-600), XTJ-502 (ED-2003), T-403, XTJ-509 (T-3000), and T-5000 (Huntsman Corporation, Houston, Tex.); and polyamide resins such as the VERSAMID series of resins that are formed by reacting a dimerized unsaturated fatty acid with alkylene diamines (Cognis Corporation, Cincinnati, Ohio).

The coagulant may be prepared by condensation of the polyamine polymer with a guanylating agent. Known guanylating agents include: cyanamide; O-alkylisourea salts such as O-methylisourea sulfate, O-methylisourea hydrogen sulfate, O-methylisourea acetate, O-ethylisourea hydrogen sulfate, and O-ethylisourea hydrochloride; chloroformamidine hydrochloride; 1-amidino-1,2,4-triazole hydrochloride; 3,5-dimethylpyrazole-1-carboxamidine nitrate; pyrazole-1-carboxamidine hydrochloride; N-amidinopyrazole-1-carboxamidine hydrochloride; and carbodiimides, such as dicyclohexylcarbodiimide, N-ethyl-N'-(3-dimethylaminopropyl) carbodiimide, and diisopropylcarbodiimide. The polyamine polymer may also be acylated with guanidino-functional carboxylic acids such as guanidinoacetic acid and 4-guanidinobutyric acid in the presence of activating agents such as EDC (N-[3-(dimethylamino)propyl]-3-ethylcarbodiimide hydrochloride), or EEDQ (2-ethoxy-1-ethoxycarbonyl-1,2-dihydroquinoline). Additionally, the cationic polymer may be prepared by alkylation with chloroacetone guanyl hydrazone, as described in U.S. Pat. No. 5,712,027.

Reagents for the preparation of biguanide-functional polymers include sodium dicyanamide, dicyanodiamide and substituted cyanoguanidines such as $N^3$-p-chlorophenyl-$N^1$-cyanoguanidine, phenyl-$N^1$-cyanoguanidine, $N^3$-alpha-naphthyl-$N^1$-cyanoguanidine, $N^3$-methyl-$N^1$-cyanoguanidine, $N^3,N^3$-dimethyl-$N^1$-cyanoguanidine, $N^3$-(2-hydroxyethyl)-$N^1$-cyanoguanidine, and $N^3$-butyl-$N^1$-cyanoguanidine. Alkylene- and arylenebiscyanoguanidines may be utilized to prepare biguanide functional polymers by chain extension reactions. The preparation of cyanoguanidines and biscyanoguanidines is described in detail in Rose, F. L. and Swain, G. J. Chem Soc., 1956, pp. 4422-4425. Other useful guanylating reagents are described by Alan R. Katritzky et al., *Comprehensive Organic Functional Group Transformation*, Vol. 6, p. 640. Generally, such guanylation reagents are used in amounts sufficient to functionalize 0.5 to 100 mole percent, preferably 2.5 to 50 mole percent, of the available amino groups of the aminopolymer. The resulting polymer will have pendent or catenary guanidinyl groups of the formula III:

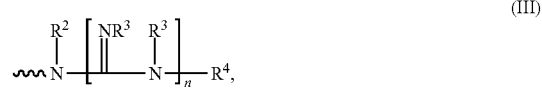

(III)

wherein
$R^2$ is a H, $C_1$-$C_{12}$ alkyl, $C_5$-$C_{12}$ (hetero)aryl, or a residue of the polymer chain;
each $R^3$ is independently H, $C_1$-$C_{12}$ alkyl, or $C_5$-$C_{12}$ (hetero)aryl,
each $R^4$ is H, $C_1$-$C_{12}$ alkyl or alkylene, $C_5$-$C_{12}$ (hetero)aryl or (hetero)arylene, cyano, or —C(=NH)—N($R^2$)—Polymer, and
n is 1 or 2.

The guanidinyl-containing polymer can be crosslinked. The amino-containing polymer can be crosslinked prior to reaction with the guanylating agent. Alternatively, the guanidinyl-containing polymer can be crosslined by reaction of a crosslinker with remaining amino groups from the amino-containing polymer precursor or with some of the guanidinyl groups. Suitable crosslinkers include amine-reactive compounds such as bis- and polyaldehydes such as glutaraldehyde, bis- and polygylcidylethers such as butanedioldiglycidylether and ethyleneglycoldiglycidylether, polycarboxylic acids and their derivatives (e.g., acid chlorides), polyisocyanates, formaldehyde-based crosslinkers such as hydroxymethyl and alkoxymethyl functional crosslinkers, such as those derived from urea or melamine, and amine-reactive silanes, such as 3-glycidoxypropyltrimethoxysilane, 3-glycidoxypropyltriethoxysilane, 5,6-epoxyhexyltriethoxysilane, (p-chloromethyl)phenyltrimethoxysilane, chloromethyltriethoxysilane, 3-isocyanatopropyltriethoxysilane, and 3-thiocyanatopropyltriethoxysilane.

In other embodiments, the gel composition comprises a hemostatic agent, such as a polymerizable cyanoacrylate monomer. Other coagulants include microfibrillar collagen, chitosan, bone wax, ostene, oxidized cellulose and thrombin.

If included, coagulants are typically present in quantities of at least 0.5 wt. % and no greater than 20 wt. %, based on the total weight of the gel composition, or any amount within that range. In certain implementations, it may be preferred that the coagulant is present at a concentration of at least 1 wt. % and no greater than 15 wt. %, and in yet other embodiments at least 1.5 wt. % and no greater than 10 wt. %, based on the total weight of the gel composition, or any amount within that range.

A dried film cast form the gel composition may include an amount of coagulant in a range from 5 wt. % to 30 or 35 wt. % relative to a total weight of the dried film, or any amount within that range. In certain circumstances and depending on particle size, the coagulant may remain in the film during treatment, at the surface thereof, may migrate into the wound or target area to assist for localized coagulation, or some combination thereof. The film can act, in these circumstances, as a coagulant delivery system to the underlying target area.

If a silicone containing film forming polymer is used, a silicone surfactant may be incorporated to assist in stabilizing the coagulant in the gel composition. Silicone surfactants typically include polydimethylsiloxane (PDMS) fluids and/or organomodified PDMS fluids such as siloxane polyether copolymers. One exemplary suitable PDMS surfactant is a monocarboyxldecyl terminated polydimethylsiloxane, (available as MCR-B-12 from Gelest LTD, Kent, UK). Other suitable PDMS surfactants include Abil Quat 3272, available from Evonik Goldschmidt, Germany. Another suitable surfactant is dimethoxymethylsilylpropyl-polyethylene Imine—50% in IPA, available from Gelest. In certain circumstances, the silicone surfactant can improve adhesion of the gel (and the resultant dried film) to tissue.

If included, silicone surfactants are typically present in quantities of at least 0.1 wt. % and no greater than 15 wt. %, based on the total weight of the gel composition. A dried film cast from the gel composition may include an amount of silicone surfactant in a range from 1 wt. % to 15 or 20 wt. % relative to a total weight of the dried film, or any amount within that range.

In certain formulations that feature a guanidinyl-containing polymer as a coagulant, it can be useful to include a relatively small amount of silicone surfactant or none at all. In such compositions, the silicone surfactant is present in quantities of no greater than 0.25 wt. %, based on the total weight of the gel composition. Applicants have found some evidence that, in contrast to the expected stabilization, the inclusion of greater than 0.25 wt. % can (in certain circumstances) decrease the stability of the composition over an otherwise expected storage life.

Solvent

The coating gel composition further comprises a volatile solvent. In one embodiment, the volatile solvent is selected from the group consisting of volatile linear and cyclic siloxanes, volatile polydimethylsiloxanes, isooctane, octane, and combinations thereof. The solvent is typically at least 40 wt. % of the total gel composition. As the composition may be applied to tissue, the solvent is desirably volatile and non-stinging. In one embodiment, at least 60 wt. % of the total composition is the solvent. In yet other embodiments, the solvent is present in at least 70 wt. % of the total composition.

The solvent system for the gel compositions of the present disclosure can be a non-polar, volatile solvent such as isooctane. Other exemplary volatile solvent systems include a linear siloxane or a cyclic siloxane, such as hexamethyldisiloxane (HMDS), octamethylcyclotetrasiloxane, decamethylcyclopentasiloxane, and octamethyltrisiloxane, or a linear, branched or cyclic alkane, such as propane, isobutane, liquid butane (e.g., under pressure), pentane, hexane, heptane, octane, petroleum distillates, cyclohexane, fluorocarbons, such as trichloromonofluoromethane, dichlorodifluoromethane, dichlorotetrafluoroethane, tetrafluoroethane, heptafluoropropane, 1,1-difluoroethane, pentafluoropropane, perfluoroheptane, perfluoromethylcyclohexane, 1,1,1,2,-tetrafluoroethane, 1,1,1,2,3,3,3-heptafluoropropane, chlorofluorocarbons, in addition to liquid carbon dioxide, and combinations thereof. As used herein, "volatile" has its standard meaning, that is, it can evaporate rapidly at normal temperatures and pressure. For example, a solvent can be volatile if one metric drop (½₀ mL, 50 mu L) of the solvent will evaporate completely between 20-25° C. within 5 minutes, or within 4 minutes, or within 3 minutes, or within 2 minutes, or within 1 minute, or within 30 sec, or within 15 sec.

The use of non-polar, volatile solvents, alone or in combination, as the primary liquid phase of the gel composition can provide a desirable balance between fast drying and reduced skin irritation during application. In presently preferred implementations, the solvent is one of HMDS and isooctane. Other, more polar solvents such as ethanol, isopropanol, glycerin, N-methylpyrrolidone, and N,N-dimethylacetamide can be used in other implementations, where a non-stinging gel composition is either unnecessary or undesirable. Numerous aprotic solvents have utility including acetates such as methyl and ethyl acetate, propylene glycol diacetate, volatile ketones such as acetone and methyl ethyl ketone, volatile ethers such as diethyl ether, ethyl propyl ether, dipropyl ether and dipropylene glycol dimethyl ether, volatile fluorocarbons, such as pentafluoropropane, perfluoroheptane, perfluoromethylcyclohexane and the like; or a volatile gas, such as carbon dioxide, can also be employed, each with varying degrees of user discomfort.

In some implementations, water may be included in a solvent system, which can be useful in solublizing certain active agents and hemostats. In certain implementations, a relatively small amount of water is present in the gel composition, such as at least 0.1 wt. %, based on the total weight of the composition. In other embodiments, the water content is at least 60 wt. %, based on the total weight of the composition, though such composition may require longer dry times than presently desired. Certain solvent systems including water are exemplified in U.S. Pat. No. 7,651,990 (Asmus), and U.S. Pat. No. 8,338,491 (Asmus et al.).

Additives

The gel compositions of the present disclosure may include filler. Examples of suitable fillers are naturally occurring or synthetic materials including, but not limited to: quartz (i.e., silica, $SiO_2$); nitrides (e.g., silicon nitride); glasses and fillers derived from, for example, Zr, Sr, Ce, Sb, Sn, Ba, Zn, and Al; feldspar; borosilicate glass; kaolin (china clay); talc; zirconia; titania; and submicron silica particles (e.g., pyrogenic silicas such as those available under the trade designations AEROSIL, including "OX 50," "130," "150" and "200" silicas from Degussa Corp., Akron, Ohio and CAB-O-SIL M5 and TS-720 silica from Cabot Corp., Tuscola, Ill.). Organic fillers made from polymeric materials are also possible, such as disclosed in PCT Publication No. WO09/045752 (Kalgutkar et al.).

Clay materials suitable for use in compositions, methods, and articles of the present disclosure can include those in the geological classes of the smectites, the kaolins, the illites, the chlorites, the serpentines, the attapulgites, the palygorskites, the vermiculites, the glauconites, the sepiolites, and the mixed layer clays. Smectites, for example, can include montmorillonite, bentonite, pyrophyllite, hectorite, saponite, sauconite, nontronite, talc, beidellite, and volchonskoite. Kaolins, for example, can include kaolinite, dickite, nacrite, antigorite, anauxite, halloysite, indellite and chrysotile. Illites, for example, include bravaisite, muscovite, paragonite, phlogopite and biotite. Chlorites, for example, can include corrensite, penninite, donbassite, sudoite, pennine and clinochlore. Mixed layer clays, for example, can include allevardite and vermiculitebiotite. Variants and isomorphic substitutions of these layered clay minerals offer unique applications.

A typical gel composition of the present disclosure includes at least one of kaolin and fumed silica. In certain implementations, the inclusion of fumed silica can enhance the ability of the gel composition to form a substantially level film surface and ease of removing the dried film by peel. Appropriate amounts of filler will be familiar to those skilled in the art, and will depend upon numerous factors including, for example, the polymer(s) utilized, the type of filler, and the intended treatment area(s) of the gel composition. Typically, filler will be added at a level of about 1% to about 20% by weight (preferably, about 3% to about 15% by weight), based upon the total weight of the gel composition, or any amount within that range. A dried film cast form the gel composition may include an amount of filler in a range from 0.1 wt. % to 30 wt. % relative to a total weight of the dried film, or any amount within that range.

If biocidal (or in certain implementations bacteriostatic) properties are desired, antiseptic and/or antibiotic agents may be suspended or otherwise dispersed in the gel composition. In some implementations, the antiseptic is a cationic antimicrobial agent including an effective amount of one or more antimicrobial agents selected from the group consisting of biguanides and bisbiguanides such as chlorhexidine, alexidine, and their various salts including but not limited to the digluconate, diacetate, dimethosulfate, and dilactate salts, as well as combinations thereof polymeric cationic ammonium compounds such as polyhexamethylenebiguanide salts; small molecule quaternary ammonium compounds such as benzalkonium halides; cationic antimicrobial dyes; and compatible combinations thereof.

Particularly useful cationic antimicrobial agents include benzalkonium chloride, chlorhexidine gluconate, octenidine dihydrochloride, cetyl pyridinium chloride, cetrimonium bromide, benzethonium chloride, polyhexamethylene biguanide salt, methylene blue, toluidiene blue, cationic dyes and compatible combinations thereof. Additional details regarding exemplary cationic antimicrobial agents may be found in International Publication No. WO2014/008264 (Parthasarathy et al.)

The antiseptic agent is typically added to the composition at a concentration of at least 0.01 wt. %, in some embodiments at least 0.05 wt. %, in some embodiments at least 0.1 wt. %, in some embodiments at least 0.2 wt. %, in some embodiments at least 0.5 wt. %, in other embodiments at least 0.6 wt. %, in yet other embodiments at least 1.0 wt. % and in yet other implementations at least 1.5 wt. %, in some cases exceeding 2 wt. %., based on the total weight of the gel composition. Preferably, the composition comprises not greater than 10 wt. %, more preferably no greater than 8 wt. %, and most preferably no greater than 5 wt. %. A potential range for antiseptic agent concentration to enhance active kill is at least 0.1 wt. % and no greater than 1.0 wt. %, based on the total weight of the composition. A dried film cast form the gel composition may include an amount of antiseptic agent in a range from 0.1 wt. % to 4 wt. % relative to a total weight of the dried film, or any amount within that range. It should be appreciated that the above concentrations relate to the total amount of cationic agent in the composition, even if a plurality of cationic antimicrobial agents are used.

In certain embodiments, the gel composition can have a synergistic antimicrobial effective amount of an antiseptic surfactants, particularly straight chain 1,2-alkanediols having a chain length in the range of 5 to 10 carbon atoms. Such 1,2-alkanediols include, 1,2-pentanediol, 1,2-hexanediol, 1,2-heptanediol, 1,2-octanediol, 1,2-nonanediol, and 1,2-decanediol, and combinations thereof. One exemplary suitable 1,2-octanediol composition includes 3-[(2-ethylhexyl) oxy]-1,2-propanediol, and is sold as SENSIVA SC-10 by Schülke&Mayr GmbH, Germany. Without wishing to be bound by theory, the inclusion of straight chain 1,2-alkanediols can reduce the tendency of certain cationic antimicrobial agents (e.g., benzethonium chloride) to crystallize in a dried film. By preventing or otherwise reducing the tendency to crystallize, the straight chain 1,2-alkanediols can prolong the availability of the antimicrobial agent, in that the active kill time is enhanced. A dried film cast form the gel composition may include an amount of antiseptic surfactant in a range from 0.5 wt. % to 2 wt. % relative to a total weight of the dried film, or any amount within that range.

A particularly cogent property of certain gel compositions including an antiseptic agent is the ability to reduce the bacterial load on tissue, particularly skin (e.g., to kill the natural skin flora). In certain embodiments, the dried film achieves at least 1 log reduction of a target microorganism in 2 hours when evaluated by the Antimicrobial Efficacy Test described below. In more desirable embodiments, the compositions achieve a 2 log reduction. In even more desirable embodiments, the compositions achieve a 3 log reduction. In certain embodiments, the target organisms comprise *Pseudomonas aeruginosa, Staphylococcus aureus, Escherichia coli*, and methicillin-resistant *Staphylococcus aureus*. In certain embodiments, residual antimicrobial efficacy is provided to any surface formed from the dried gel composition. In certain embodiments, the dried film provides an active kill for an extended period of time during the life of the film.

Other anti-infective agents, such as nano-silver particles and silver sulfadiazine, may also be added to gel compositions of the present invention. Such anti-infective agents can be added as suspended solids to the coating polymer in the volatile solvent. Topical antibiotics such as neomycin, polymyxin B, and bacitracin can also be included. Other solid biologically active materials, such as anti-itch agents, such as chamomile, *eucalyptus*, camphor, menthol, zinc oxide, talc, and calamine, anti-inflammatory agents, such as corticosteroids, antifungal agents, such as terbinafine hydrochloride and miconazole nitrate, and non-steriodal anti-inflammatory agents, such as ibuprofen, can be added in like fashion. Essential oils can also be added as flavoring agents, aromatic agents, or antimicrobial agents, including thymol, menthol, sandalwood, cinnamon, jasmine, lavender, pine, lemon, rose, *eucalyptus*, clove, orange, mint, spearmint, peppermint, lemongrass, bergamot, citronella, cypress, nutmeg, spruce, tea tree, wintergreen, vanilla, and the like. After evaporation of the volatile, solvent, the dried film may contain entrapped active biological or pharmaceutical ingredients for controlled release to a biological surface.

Other exemplary antimicrobials agents useful as antiseptics include phenolic antiseptics such as parachlorometaxylenol (PCMX), triclosan, hexachlorophene, and others disclosed in U.S. Pat. No. 8,198,326 (Scholz); fatty acid monoesters of glycerin and propylene glycol such as glycerol monolaurate, glycerol monocaprylate, glycerol monocaprate, propylene glycol monolaurate, propylene glycol monocaprylate, propylene glycol moncaprate, $C_8$-$C_{12}$ alkyl monoethers of glycerin and propylene glycol such as 2-ethylhexyl glycerin ether (available from Schuelke Mayr, Norderstedt, Germany, under the trade designation "SENSIVA SC 50"), natural oil antiseptics; $C_6$-$C_{12}$ alkyl and aryl carboxylic acids; quaternary silanes, silver, silver salts such as silver chloride, silver oxide silver sulfadiazine, copper, copper salts, and combinations thereof.

Other examples of actives agents (or drugs) that can be incorporated into the gel compositions of the present disclosure are those capable of local or systemic effect when administered to the skin. Some examples include buprenorphine, clonidine, diclofenac, estradiol, granisetron, isosorbide dinitrate, levonorgestrel, lidocaine, methylphenidate, nicotine, nitroglycerine, oxybutynin, rivastigmine, rotigotine, scopolamine, selegiline, testosterone, tulobuterol, and fentanyl. Other examples include, but are not limited to, antiinflammatory drugs, both steroidal (e.g., hydrocortisone, prednisolone, triamcinolone) and nonsteroidal (e.g., naproxen, piroxicam); bacteriostatic agents (e.g., chlorhexidine, hexylresorcinol); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotazoals (e.g., metronidazole); antifungals (e.g., nystatin); coronary vasodilators; calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, acetylcholinesterase inhibitors (e.g., donepezil), elastase inhibitors, lipoxygenase inhibitors (e.g., A64077), and angiotensin converting enzyme inhibitors (e.g., captopril, lisinopril); other antihypertensives (e.g., propranolol); leukotriene antagonists (e.g., ICI204,219); anti-ulceratives such as H2 antagonists; steroidal hormones (e.g., progesterone); antivirals and/or immunomodulators (e.g., 1-isobutyl-1H-imidazo[4,5-c]quinolin-4-amine, 1-(2-hydroxy-2-methyl-propyl)-1H-imidazo[4,5-c]quinolin-4-amine, N-[4-(4-amino-2-ethyl-1H-imidazo[4,5-c]quinolin-1-yl)butyl] methanesulfonamide, and acyclovir); local anesthetics (e.g., benzocaine, propofol, tetracaine, prilocaine); cardiotonics (e.g., digitalis, digoxin); antitussives (e.g., codeine, dextromethorphan); antihistamines (e.g., diphenhydramine, chlorpheniramine, terfenadine); narcotic analgesics (e.g., morphine, fentanyl citrate, sufentanil, hydromorphone hydrochloride); peptide hormones (e.g., human or animal growth hormones, LHRH, parathyroid hormones); cardioactive products such as atriopeptides; antidiabetic agents (e.g., insulin, exanatide); enzymes (e.g., anti-plaque enzymes, lysozyme, dextranase); antinauseants; anticonvulsants (e.g., carbamazine); immunosuppressives (e.g., cyclosporine); psychotherapeutics (e.g., diazepam); sedatives (e.g., phenobarbital); anticoagulants (e.g., heparin, enoxaparin sodium); analgesics (e.g., acetaminophen, camphor, lidocaine, and others listed in 21 C.F.R 348.10, Analgesic, anesthetic, and antiprunitic active ingredients (Apr. 1, 2012)); antimigraine agents (e.g., ergotamine, melatonin, sumatriptan, zolmitriptan); antiarrhythmic agents (e.g., flecainide); antiemetics (e.g., metaclopromide, ondansetron, granisetron hydrochloride); anticancer agents (e.g., methotrexate); neurologic agents such as anxiolytic drugs; anti-obesity agents; dopamine agonists (e.g., apomorphine); GnRH agonists (e.g., leuprolide, goserelin, nafarelin); fertility hormones (e.g., hCG, hMG, urofollitropin); interferons (e.g., interferon-alpha, interferon-beta, interferon-gamma, pegylated interferon-alpha); and the like, as well as pharmaceutically acceptable salts and esters thereof.

The compositions may further contain fibrous reinforcement and colorants such as dyes, pigments, and pigment dyes. Examples of suitable fibrous reinforcement include PGA microfibrils, collagen microfibrils, and others as described in U.S. Pat. No. 6,183,593. Examples of suitable colorants as described in U.S. Pat. No. 5,981,621 include 1-hydroxy-4-[4-methylphenylamino]-9,10-anthracenedione (FD&C violet No. 2); disodium salt of 6-hydroxy-5-[(4-sulfophenyl)oxo]-2-naphthalenesulfonic acid (FD&C Yellow No. 6); 9-(o-carboxyphenyl)-6-hydroxy-2,4,5,7-tetraiodo-3H-xanthen-3-one, disodium salt, monohydrate (FD&C Red No. 3); and the like.

The use of florescent dyes and pigments can also be beneficial in enabling the coating to be viewed under blacklight. The coating could be substantially clear and transparent under normal lighting so the site can be easily viewed and inspected for changes in the skin. As a means of ensuring the coating is intact and covering the desired area, the site can be inspected by the use of a backlight wand or flashlight which reveals the coating by its florescence. A particularly useful hydrocarbon soluble fluorescing dye is 2,5-bis(5-tert-butyl-2-benzoxazolyl) 1 thiophene. Fluorescing dyes, such as rhodamine, may also be bound to cationic polymers and incorporated as part of the coagulant.

Kits

The gel compositions of the present disclosure may advantageously be provided in a kit. The kit may contain an applicator, a wound cleaning solution, and an absorbent material. In some implementations, the gel composition is arranged in the kit in a vial or other rupturable package separate from the applicator. In other implementations, the applicator is pre-loaded with the gel composition (e.g., in a delivery reservoir).

Methods of Application and Removal

A treatment protocol may involve skin preparation prior to applying the gel compositions of the present disclosure. The target site is preferably dried, e.g., blotted dry, and then a lightly adherent polymeric film is formed over this site by applying the gel composition.

Sufficient amounts of the composition are employed to cover (i.e., coat) the entire target site with a layer of the gel composition. It is typically preferred that the resultant dried film have a thickness from about 4 to about 15 mills. The resultant film typically covers at least the entire area of the wound or other target site, but may not under other circumstances. If necessary, excess gel can be removed with a wipe or tissue paper before drying.

The gel composition can applied from a single dose product or by use of a multiple use dispenser which governs the amount of material applied onto a unit area. In this regard, the dispenser described in U.S. Pat. No. 5,558,560 (Benedict), is one example of a dispenser suitable for dispensing a viscous composition through use of a squeeze-tube and applicator tip. In presently preferred circumstances, the dispenser is suited for dispensing a gel composition having a viscosity of 200,000 to 500,000 cps (particularly 250,000 to 400,000 cps) and a wet coat weight of 50 to 120 mils at a generally uniform thickness. Other methods for the controlled dispersal of the gel composition include, by way of example, a spray applicator, brush, wipe, swab or solid paddle applicator, applicators for repeated and intermittent use of the gel composition and the like. In most applicators (e.g., those featuring a dispensing tip and a squeeze-tube), the gel composition can be conveniently stored at ambient conditions and can be provided in sterile form.

One suitable method 10 for applying the gel composition to the wound or other target site (e.g., abrasions, lacerations, scrapes, punctures, and burns) using an applicator is set out in FIG. 1. At the outset at least the area around the target site is cleaned and dried (Step 20). Due to the conformability and breathability of the dried films of the present disclosure, drying the wound itself can be optional, depending on the amount of fluid exiting the wound site. In certain embodiments, a dried film may retain up to 1 mL of blood or exudate without detaching from the body. For moderate to severe bleeding wounds, the site is typically cleaned and dried prior to application. A first quantity of gel composition in an applicator 12 is dispensed at an area proximate the target site 11 and a substantially continuous layer 13 of the gel composition is created by drawing the applicator across the target site 11 while dispensing the composition from the tip 14 (Step 30). In certain circumstances, it may be desirable to hold the applicator tip 14 above the target site without making contact with the tissue. Such vertical displacement may not be required for minor scrapes or skin lesions. Once the layer 13 reaches an area proximate the target site (e.g., one spaced from the wound) the applicator is manipulated to sever the connection between the layer 13 and the applicator tip. (Step 40). The user may also sever the connection by hand or other tool. In certain implementations, the layer 13 possesses dimensions sufficient to entirely cover the target site. Multiple layers, however, may be used for larger wounds or smaller applicator tips. In one exemplary implementation, the continuous layer 13 has a substantially continuous thickness of about 100 mil as applied. Once the desired amount of gel is dispensed, the composition is allowed to dry to a film (typically 2-5 minutes).

Figure 2:
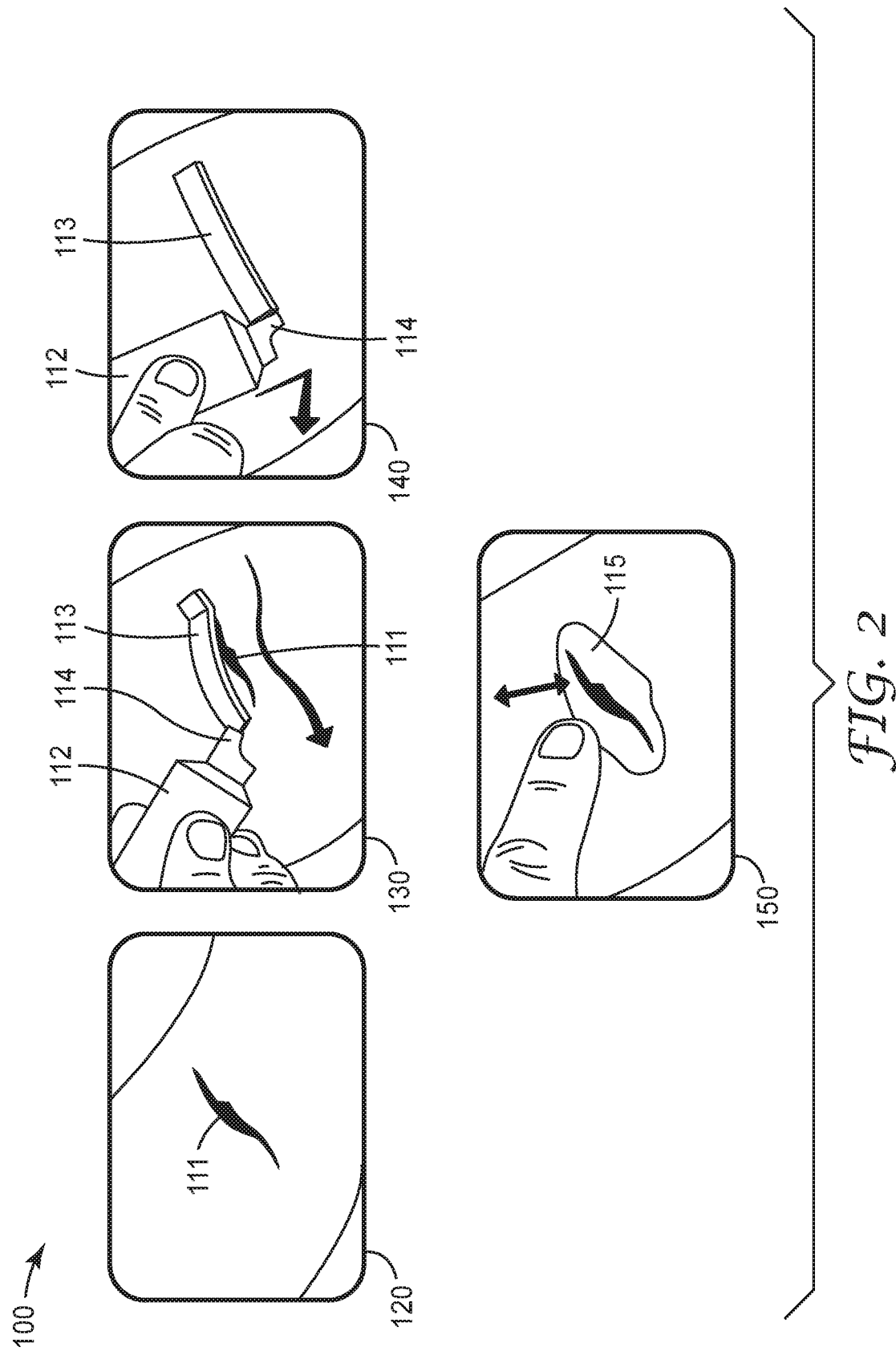
FIG. 2 is a flow chart of another method of applying a gel composition of the present disclosure to a target site.

Another suitable method for applying the gel composition to a target site using an applicator is set out in FIG. 2. Like the method 10 of FIG. 1, the method 100 of FIG. 2 includes the steps of a) cleaning and dry at least the area around the target site (Step 120); dispensing a first quantity of gel composition at an area proximate the target site 110 and creating a substantially continuous layer 113 of the gel composition by drawing the applicator across the target site 110 while dispensing the composition (Step 130) and severing the connection between the layer 113 and the applicator tip 114. (Step 140). After a period of time sufficient for the composition to form a film 115 that is dry to the touch (typically 1 to 2 minutes), the user (or treating professional) may tap the film around the periphery of the target to effect and enhance a seal around the target. (Step 150). In some embodiments, it may be desirable for the person intending to touch the film to first dampening his or her finger. Alternatively, the user (or treating professional) may wet the finger surface with a topical antiseptic or antibiotic composition for increased protection against infection or contamination. In lieu of finger pressure, surface depressing tools may be used such as Q-tips, tongue depressors, and foam applicators.

Figure 3:
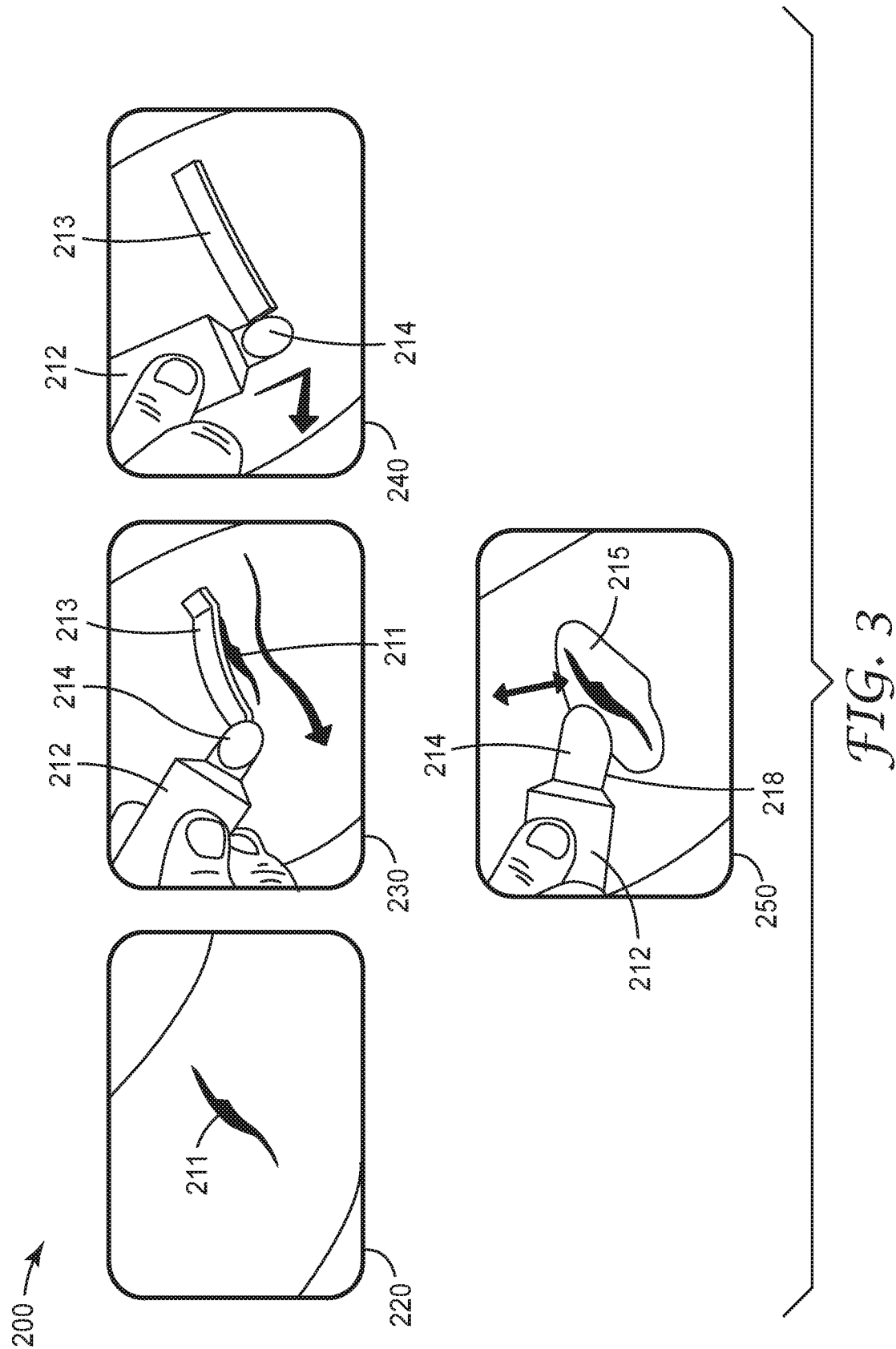
FIG. 3 is a flow chart of another method of applying a gel composition of the present disclosure to a target site.

One such tool is used in the method 200 depicted in FIG. 3. Like the method 100 of FIG. 2, the method 200 includes the steps of a) cleaning and dry at least the area around the target site (Step 220); dispensing a first quantity of gel composition at an area proximate the target site 210 and creating a substantially continuous layer 213 of the gel composition by drawing an applicator 212 across the target site 210 while dispensing the composition (Step 230) and severing the connection between the layer 213 and the applicator tip 214. (Step 240). Applicator tip 214 includes a convex surface 218 adjacent the dispensing slot. Instead of finger pressure, the user (or treating professional) may tap the film around the periphery using the convex surface 218 of the applicator. (Step 250). Using an applicator tip in this fashion may be advantageous for certain users and wound types, as the perceived (or actual) contamination attendant use of one's finger may be eliminated.

Figure 4:
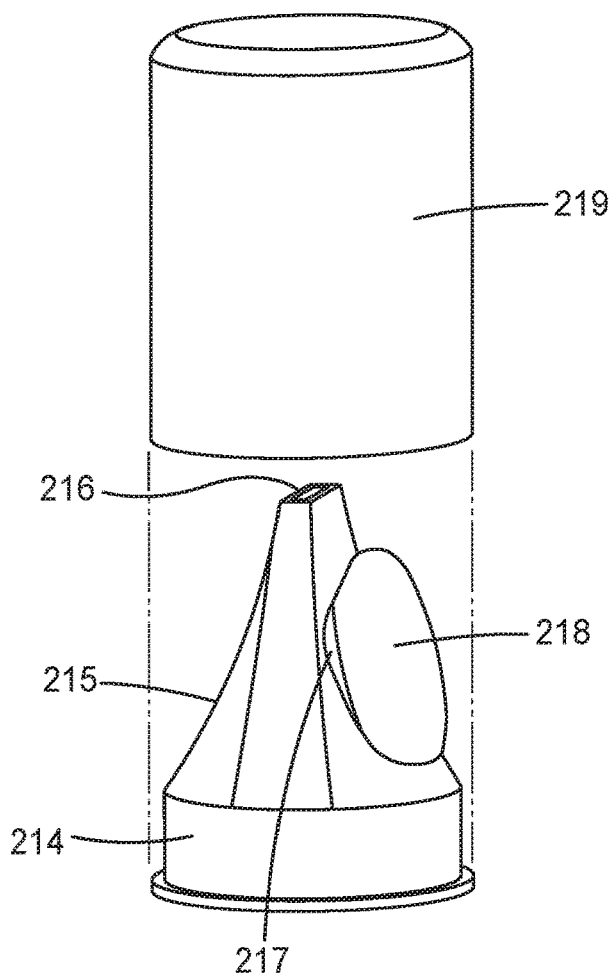
FIG. 4 is an isometric view of an applicator tip suitable for dispensing gel compositions according to methods of the present disclosure.
Figure 5:
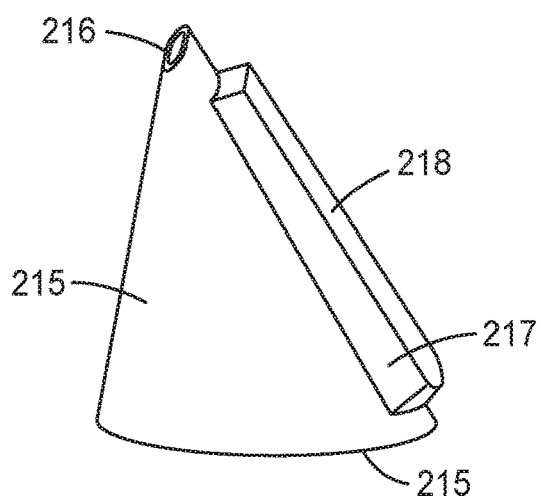
FIG. 5 is an isometric view of another applicator tip suitable for dispensing gel compositions according to methods of the present disclosure.

Suitable applicator tips for applying pressure to the gel composition or film are depicted in FIGS. 4 and 5. Each applicator tip 214 includes a generally frustoconical body 215 having a dispensing slot 216 positioned towards the top (as oriented) of the tip 214. The dispensing slot 216 is dimensioned to dispense a gel composition having a viscosity of 200,000 to 400,000 cps and a wet coat weight of 50 to 120 mils at a generally uniform thickness. The dispensing slot 216 can be disposed at an acute or obtuse angle relative to the plane defined by the bottom-most surfaces of the body 214. In other implementations, the dispensing slot can be generally parallel to a plane defined by the bottom most surfaces of the body 214. A ridge 217 projects outwardly from the body 215, displacing a surface 218 away from the body 215. The displaced outer surface 218 allows for the applicator tip 214 to be pressed into a gel composition or film without contacting the dispensing slot 215. The outer surface 218 can include a lens-like, convex structure (FIG. 4) or a rail like, planar structure (FIG. 5). One skilled in the art will recognize that other geometries and configurations are possible for surface 218, as well as applicator tip body 215. The applicator tip 214 may be supplied with or without a cap 219 used to cover the dispensing slot when the applicator is not in use.

Figure 6:
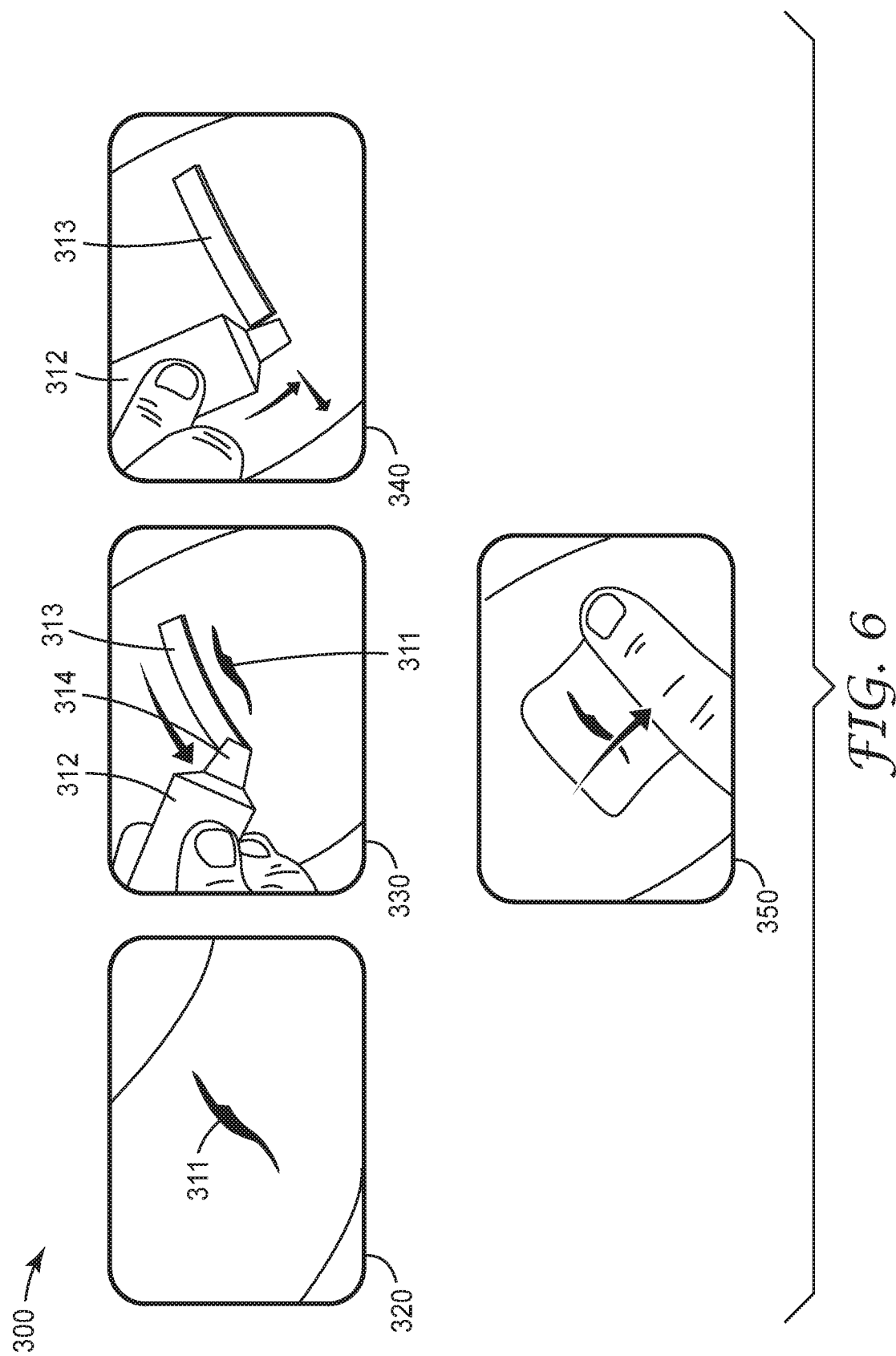
FIG. 6 is a flow chart of another method of applying a gel composition of the present disclosure to a target site.

Yet another suitable method 300 for applying a gel composition of the present disclosure to a target site is disclosed in FIG. 6. While at least the area surrounding the target is again dried, the substantially continuous layer 313 is not drawn over the target. Instead, in Step 330, a first quantity of gel composition is dispensed at an area proximate the target site 311 and a substantially continuous layer 313 of the gel composition is created by drawing the applicator along the periphery of the target site the target site 311 while dispensing the composition from the tip 314. After severing the connection between the layer and the applicator (Step 340), the resulting layer 313 is drawn across the target site and pressed on the opposite side of the target site from the original location of layer 313. (Step 350). The composition can be drawn by hand (as depicted) or by suitable tool.

The gel composition need not be applied in direct contact with the entire target site. In certain implementations, the gel composition may be applied over an antiseptic or antimicrobial composition, sutures, gauze, other topical compositions, and combinations thereof.

As referenced above, the applied gel compositions of the present disclosure can be removed with relatively little force in a single continuous film without substantial desquamation of the underlying tissue. This desirable property can be enhanced by rolling the edges of the applied film toward the center of the target (or film itself) prior to removal. Rolling can, in certain circumstances, provide a graspable edge for a user or treating professional to engage and remove the film from the skin. For thinner films (e.g., less than 4 mils), it may be sufficient for the film to be removed in multiple pieces.

EMBODIMENTS

1. A film forming gel composition for use as a conformable film bandage, the composition comprising:
    a silicone containing polymer;
    a tackifier comprising a silicate tackifying resin;
    a coagulant comprising a cationic polymer;
    and a volatile solvent, wherein a film cast from the composition is self-supporting on a biological substrate and can be peeled off the substrate without substantially compromising the integrity of the film or the substrate.

2. The composition of embodiment 1, comprising a) 10-25 wt. % film forming polymer, (b) 3-6 wt. % tackifier, (c) 60-80 wt. % volatile solvent, (d) 0.5-6 wt. % cationic polymer, and (e) 0.5-2 wt. % silicone surfactant, based on the total weight of the gel composition.

3. The composition of embodiment 1, wherein the silicone is selected from the group consisting of polydiorganosiloxane polyurea, polydiorganosiloxane polyamine, polysiloxane carbonate, polydiorganosiloxane polyamide, and combinations thereof.

4. The composition of embodiment 2, where in the polydiorganosiloxane polyamide is a polydiorganosiloxane polyoxamide.

5. The composition of any of the previous embodiments, wherein the silicone containing polymer comprises at least 12 and no greater than 25 wt %, based on the total weight of the gel composition.

6. The composition of embodiments 1-5, wherein the coagulant comprises a guanidinyl-containing polymer.

7. The composition of embodiment 6, wherein the guanidinyl-containing polymer is an aminopolymer functionalized with one or more guanidinyl groups.

8. The composition of embodiment 7, wherein the amino polymer is selected from the group consisting of polyethylenimine, polylysine, polyaminoamides, polyallylamine, polyvinylamine, polydimethylamine-epichlorohydrin-ethylenediamine, polyaminosiloxanes and dendrimers formed from polyamidoamine (PAMAM) and polypropylenimine.

9. The composition of embodiment 6, wherein the guanidinyl-containing polymer is guanidinylated polyethyleneimine.

10. The composition of embodiments 6-9, wherein the guanidinyl-containing polymer is crosslinked.

11. The composition of any of the previous embodiments, wherein the silicone containing polymer and the volatile solvent define a vehicle, and wherein the coagulant is suspended in the vehicle.

12. The composition of any of the previous embodiments, wherein the coagulant comprises at least 0.5 wt. % and no greater than 10 wt % of the gel, based on the total weight of the composition.

13. The composition of any of the previous embodiments, wherein the tackifier comprises an MQ silicate tackifying resin.

14. The composition of any of the previous embodiments, wherein the tackifier is present in an amount of 3 to 15 weight percent based on the weight of the composition.

15. The composition of any of the previous embodiments and further comprising an antiseptic agent, wherein the antiseptic comprises at least one of octenidine, chlorhexidine salt, alexidine salt, polyhexamethylene biguanide salt, benzalkonium salt, cetyl pyridinium salt, cetrimonium salt, or benzethonium salt, and combinations thereof.

16. The composition of embodiment 14, wherein the antiseptic agent comprises one or more of benzalkonium chloride, chlorhexidine gluconate, octenidine dihydrochloride, cetyl pyridinium chloride, cetrimonium bromide, benzethonium chloride, polyhexamethylene biguanide salt, methylene blue, toluidiene blue, rose Bengal, crystal violet, and combinations thereof.

17. The composition of any of the preceding embodiments, wherein the antiseptic is present at no greater than 0.3 wt. %, based on the total weight of the gel composition.

18. The composition of any of the preceding embodiments, wherein the active kill of a dried film cast from the gel composition is at least 1 log reduction of a target microorganism according to the Antimicrobial Efficacy Test Method.

19. The composition of any of the preceding embodiments, wherein the active kill of a dried film cast from the gel composition is at least 3 log reduction of a target microorganism according to the Antimicrobial Efficacy Test Method.

20. The composition of embodiment 18 or 19, wherein the target microorganism is one or more of *Staphylococcus aureus, Escherichia coli*, and *Pseudomonas aeruginosa*.

21. The composition of any of the previous embodiments, wherein the composition includes an effective amount of an antiseptic surfactant, the antiseptic surfactant comprising a straight chain 1,2-alkanediols having a chain length in the range of 5 to 10 carbon atoms.

22. The composition of embodiment 20, wherein the antiseptic surfactant comprises one or more of a 1,2-pentanediol, 1,2-hexanediol, 1,2-heptanediol, 1,2-octanediol, 1,2-nonanediol, and 1,2-decanediol, and combinations thereof.

23. The composition of any of the previous embodiments, wherein the Brookfield viscosity of the composition is at least 20,000 cps and no greater than 1,100,000 cps.

24. The composition of the embodiment 20, wherein the Brookfield viscosity of the composition is at least 50,000 cps and no greater than 800,000 cps.

25. The composition of any of the previous embodiments, wherein the volatile solvent is selected from the group consisting of volatile linear and cyclic siloxanes, volatile polydimethylsiloxanes, isooctane, octane, and combinations thereof.

26. The composition of embodiment 22, wherein the volatile solvent is selected from the group consisting of isooctane, hexamethyldisiloxane, and combinations thereof.

27. The composition of any of the previous embodiments, wherein the composition further includes a silicone surfactant.

28. The composition of embodiment 22, wherein the silicone surfactant is a polydimethylsiloxane fluid.

29. A gel composition comprising:
 (a) 10-25 wt. % film forming polymer,
 (b) 3-6 wt. % tackifier
 (c) 0-0.3 wt. % antiseptic,
 (d) 0-4 wt. % filler,
 (e) 60-80 wt. % volatile solvent,
 (f) 0-6 wt. % cationic polymer, and
 (g) 0.1-2 wt. % silicone surfactant, based on the total weight of the gel composition.

30. The composition of embodiment 29, wherein the film forming polymer is selected from the group consisting of polydiorganosiloxane polyurea, polydiorganosiloxane polyamine, polysiloxane carbonate, polydiorganosiloxane polyamide, and combinations thereof.

31. The composition of embodiment 30, where in the polydiorganosiloxane polyamide is a polydiorganosiloxane polyoxamide.

32. The composition of embodiments 29-31, wherein the coagulant comprises a guanidinyl-containing aminopolymer.

33. The composition of embodiment 32, wherein the guanidinyl-containing amino polymer is guanidinylated polyethyleneimine.

34. The composition of embodiments 33, wherein the guanidinyl-containing amino polymer is crosslinked.

35. The composition of any of the previous embodiments, wherein the tackifier comprises an MQ silicate tackifying resin.

36. The composition of any of the previous embodiments, wherein the antiseptic comprises one or more of benzalkonium chloride, chlorhexidine gluconate, octenidine dihydrochloride, cetyl pyridinium chloride, cetrimonium bromide, benzethonium chloride, polyhexamethylene biguanide salt, methylene blue, toluidiene blue, rose Bengal, crystal violet, and combinations thereof.

37. The composition of any of the preceding embodiments, wherein the active kill of a dried film cast from the gel composition is at least 1 log reduction of a target microorganism according to the Antimicrobial Efficacy Test Method.

38. The composition of embodiment 37, wherein the target microorganism is one or more of *Staphylococcus aureus*, *Escherichia coli*, and *Pseudomonas aeruginosa*.

39. The composition of any of the previous embodiments, wherein the composition further includes an effective amount of an antiseptic surfactant, the antiseptic surfactant comprising a straight chain 1,2-alkanediols having a chain length in the range of 5 to 10 carbon atoms.

40. The composition of any of the previous embodiments, wherein the Brookfield viscosity of the composition is at least 20,000 cps and no greater than 1,100,000 cps.

41. The composition of the embodiment 39, wherein the Brookfield viscosity of the composition is at least 50,000 cps and no greater than 800,000 cps.

42. The composition of any of the previous embodiments, wherein the volatile solvent is selected from the group consisting of isooctane, hexamethyldisiloxane, and combinations thereof.

43. A film useful as a conformable bandage, wherein the film exhibits an upright MVTR of at least 300 $g/m^2/24$ hours, a Skin Adhesion of at least 50 g/inch and no greater than 900 g/inch, an elongation of at least 100%, and an ultimate tensile strength of at least 0.3 MPa,
wherein at least a portion of the film has a thickness of at least 2 mils and no greater than 20 mils, and
wherein the film is self-supporting and consists of a single layer.

44. The film of the embodiment 43, wherein the film comprises
(a) 50-75 wt. % silicone containing, film forming polymer,
(b) 15-30 wt. % tackifier
(c) 0.1-0.5 wt. % antiseptic,
(d) 0-12 wt. % filler,
(e) 0-25 wt. % cationic polymer, and
(f) 1-15 wt. % silicone surfactant, based on the total weight of the film.

45. The composition of embodiment 44, wherein the film forming polymer is selected from the group consisting of polydiorganosiloxane polyurea, polydiorganosiloxane polyamine, polysiloxane carbonate, polydiorganosiloxane polyamide, and combinations thereof.

46. The composition of embodiment 45, where in the polydiorganosiloxane polyamide is a polydiorganosiloxane polyoxamide.

47. The composition of embodiments 44-46, wherein the cationic polymer comprises a crosslinked, guanidinyl-containing aminopolymer.

48. The composition of embodiment 47, wherein the guanidinyl-containing amino polymer is guanidinylated polyethyleneimine.

49. The composition of any of the previous embodiments, wherein the tackifier comprises an MQ silicate tackifying resin.

50. The composition of any of the previous embodiments, wherein the antiseptic comprises one or more of benzalkonium chloride, chlorhexidine gluconate, octenidine dihydrochloride, cetyl pyridinium chloride, cetrimonium bromide, benzethonium chloride, polyhexamethylene biguanide salt, methylene blue, toluidiene blue, rose Bengal, crystal violet, and combinations thereof.

51. The composition of embodiment 50, wherein the antiseptic is benzethonium chloride.

52. The composition of any of the preceding embodiments, wherein the active kill is at least 1 log reduction of a target microorganism according to the Antimicrobial Efficacy Test Method.

53. The composition of embodiment 52, wherein the target microorganism is one or more of *Staphylococcus aureus*, *Escherichia coli*, and *Pseudomonas aeruginosa*.

54. The film of any of the previous embodiments, wherein the film further includes an effective amount of an antiseptic surfactant, the antiseptic surfactant comprising one or more of a 1,2-pentanediol, 1,2-hexanediol, 1,2-heptanediol, 1,2-octanediol, 1,2-nonanediol, and 1,2-decanediol, and combinations thereof.

55. The film of any of the previous embodiments, wherein the composition further includes a silicone surfactant.

56. The film of any of the previous embodiments, wherein the film exhibits an Upright MVTR of at least 1000 $g/m^2/24$ hours and no greater than 2500 $g/m^2/24$ hours.

57. A film forming gel composition for use as a conformable film bandage, the composition comprising: a silicone containing, film forming polymer; a tackifier comprising a silicate tackifying resin; a coagulant comprising a cationic polymer; and a volatile solvent, wherein a film cast from the composition is self-supporting on a biological substrate and can be peeled off the substrate without substantially compromising the integrity of the film such that at least a portion of the film is removable in a single continuous layer.

58. The composition of embodiment 57, comprising a) 10-30 wt. % film forming polymer, (b) 3-20 wt. % tackifier, (c) 60-80 wt. % volatile solvent, (d) 0.5-20 wt. % cationic polymer, based on the total weight of the gel composition.

59. The composition of embodiment 57 or 58, wherein the silicone is selected from the group consisting of polydiorganosiloxane polyurea, polydiorganosiloxane polyamine, polysiloxane carbonate, polydiorganosiloxane polyamide, and combinations thereof.

60. The composition of embodiment 59, wherein the polydiorganosiloxane polyamide is a polydiorganosiloxane polyoxamide.

61. The composition of any one of embodiments 57-59 and further comprising 0.1-15 wt. % silicone surfactant, based on the total weight of the gel composition.

62. The composition of any one of embodiments 57-61, wherein the coagulant comprises a guanidinyl-containing polymer.

63. The composition of embodiment 62, wherein the guanidinyl-containing polymer is aminopolymer functionalized with one or more guanidinyl groups.

64. The composition of embodiment 63, wherein the guanidinyl-containing polymer is guanidinylated polyethyleneimine.

65. The composition of any one of embodiments 62-64, wherein the guanidinyl-containing polymer is crosslinked.

66. The composition of any one of embodiments 57-65, wherein the coagulant comprises at least 1.5 wt. % and no greater than 10 wt. % of the gel, based on the total weight of the composition.

67. The composition of embodiments 57-66, wherein the tackifier comprises an MQ silicate tackifying resin.

68. The composition of any of the previous embodiments and further comprising an antiseptic agent, wherein the antiseptic comprises at least one of octenidine, chlorhexidine salt, alexidine salt, polyhexamethylene biguanide salt, benzalkonium salt, cetyl pyridinium salt, cetrimonium salt, or benzethonium salt, and combinations thereof.

69. The composition of embodiment 68, wherein the antiseptic is present at a concentration of at least 0.1 wt. % and no greater than 1.0 wt. %, based on the total weight of the composition.

70. The composition of any embodiments 68-69, wherein the active kill of a dried film cast from the gel composition is at least 3 log reduction of a target microorganism according to the Antimicrobial Efficacy Test Method, and wherein the target microorganism is one or more of *Staphylococcus aureus, Escherichia coli*, and *Pseudomonas aeruginosa*.

71. The composition of embodiments 68-70, wherein the composition includes an effective amount of an antiseptic surfactant, the antiseptic surfactant comprising a straight chain 1,2-alkanediols having a chain length in the range of 5 to 10 carbon atoms.

72. The composition of any of the previous embodiments, wherein the volatile solvent is selected from the group consisting of volatile linear and cyclic siloxanes, volatile polydimethylsiloxanes, isooctane, octane, and combinations thereof.

73. The composition of any of the previous embodiments, wherein a film cast from the composition exhibits an elongation of at least 100%, and an ultimate tensile strength of at least 0.3 MPa after drying on a biological substrate.

74. The composition of embodiment 73, wherein the film exhibits an upright MVTR of at least 300 g/m$^2$/24 hours, a Skin Adhesion of at least 50 g/inch and no greater than 900 g/inch.

75. A film useful as a conformable bandage, wherein the film exhibits an upright MVTR of at least 300 g/m$^2$/24 hours, a Skin Adhesion of at least 50 g/inch and no greater than 900 g/inch, an elongation of at least 100%, and an ultimate tensile strength of at least 0.3 MPa, wherein at least a portion of the film has a thickness of at least 2 mils and no greater than 20 mils, and wherein the film is self-supporting and consists of a single layer.

76. The film of the embodiment 75, wherein the film comprises (a) 50-75 wt. % film forming polymer, (b) 15-30 wt. % tackifier, (d) 0.1-30 wt. % filler, and optionally (e) 5-35 wt. % cationic polymer, based on the weight of the film.

77. The composition of embodiment 76, wherein the film forming polymer is a silicone containing polymer selected from the group consisting of polydiorganosiloxane polyurea, polydiorganosiloxane polyamine, polysiloxane carbonate, polydiorganosiloxane polyamide, and combinations thereof, wherein the polydiorganosiloxane polyamide is a polydiorganosiloxane polyoxamide.

78. The composition of embodiments 75-77, wherein the cationic polymer comprises a crosslinked, guanidinyl-containing aminopolymer.

79. The film of any of embodiments 75-78, wherein the film exhibits an Upright MVTR of at least 1000 g/m$^2$/24 hours and no greater than 2500 g/m$^2$/24 hours.

80. The film of any of the previous embodiments, wherein the filler is at least one of kaolin and fumed silica.

81. The film of any of the previous embodiments, and further comprising 1-15 wt. % silicone surfactant, based on the weight of the film.

Objects and advantages of this disclosure are further illustrated by the following examples, but the particular materials and amounts thereof recited in these examples, as well as other conditions and details, should not be construed to unduly limit this disclosure.

EXAMPLES

Test Methods
Viscosity Test Method

The viscosities of exemplary formulation can be measured using a Brookfield viscometer, model LVT with Brookfield LV spindles (#4). All Examples should be allowed to equilibrate at approximately 22° C. for 24 hours prior to measurement. Preferably the smallest spindle and the lowest speed are chosen such that the viscosity is taken at the lowest speed possible while staying within 10-90% and preferably 20-80% of the viscometer range. In all cases the sample size and container geometry should be chosen to ensure that there were no wall effects. By "wall effects" it is meant the viscosity value is not affected by the container and is essentially equivalent to the viscosity taken in an infinitely large container. For this reason lower viscosity samples require a larger sample size to accommodate the larger spindles. The viscosity of each sample would be taken as the highest relatively stable reading that was achieved.

Skin Adhesion Test Method

The gel compositions to be tested for skin adhesion are applied to the skin of one or more human subjects. The backs of one or more subjects are to be washed using soap (in particular, IVORY SOAP) prior to sample application. The gel composition samples are applied to a width of 2.54 cm (1.0 in.), a length of 7.62 cm (3 in.), and allowed to dry to a film thickness of at least 5 mils. Samples should be placed on the subject's back positioned so that the long axis of each sample was oriented perpendicular to the volunteer's spine. The order of application of sample materials is to be randomized (i.e., rotational placement) on each subject. Sample materials are secured using a 2 kg. (4.5-pound) roller. The samples are removed at 180 degrees at a rate of 30.5 cm/minute (12 inches per minute). The peel force is then measured with a load cell in units of grams force. An initial set of gel compositions are applied and immediately removed ("T-0"). Another set of samples are applied and allowed to dwell for 24 hours before removal ("T-24"), and another set of samples are applied and allowed to dwell for 48 hours before removal ("T-48").

Skin Stripping Test Method

The gel compositions to be tested are applied to the skin of one or more human subjects. The adhesive samples should have a width of 2.54 cm (1.0 in.) and length of 7.62 cm (3 in.) and a film thickness of at least 5 mils. Samples are to be placed on the subject's back positioned so that the long axis of each sample was oriented perpendicular to the volunteer's spine. 4 hours later, the testing sample is removed at 180 degrees at a rate of 30.5 cm/minute (12 inches per minute) and immediately covered with a fresh liner to prevent the skin facing surface of the film from contamination by hand touch or dirt/dust from environment. A random point on the surface where the sample that is then peeled off after 4 hours (T4), and is analyzed using an infrared transmissivity analyzer (ATR method). The light absorption is measured at a frequency that keratin is known to absorb in (protein) (1539 cm-1, 1630 cm-1) with the absorbance when actual skin is measured being considered 100% and the absorbance of the film alone when not applied to the skin being considered 0%, the absorbance of keratin that adhered to the surface of the adhesive is recorded as a percentage, then an average value is calculated. The samples are then tested again after a 24 hour dwell.

Moisture Vapor Transmission Rate—Upright (Dry) MVTR Method

The upright MVTR was measured according to ASTM E-96-80. A 3.8 cm diameter sample was placed between adhesive-containing surfaces of two foil adhesive rings, each having a 5.1 cm$^2$ elliptical opening. The holes of each ring were carefully aligned. Finger pressure was used to form a foil/sample/foil assembly that was flat, wrinkle free, and had no void areas in the exposed sample.

A 120-ml glass jar was filled with approximately 50 mL of tap water that contained a couple drops of 0.02% (w/w) aqueous Methylene Blue USP (Basic Blue 9, C.I. 52015) solution, unless specifically stated in an example. The jar was fitted with a screw-on cap having a 3.8 inch diameter hole in the center thereof and with a 4.45 cm diameter rubber washer having an approximately 3.6 cm hole in its center. The rubber washer was placed on the lip of the jar and foil/sample/foil assembly was placed backing side down on the rubber washer. The lid was then screwed loosely on the jar.

The assembly was placed in a chamber at 40° C. and 20% relative humidity for four hours. At the end of four hours, the cap was tightened inside the chamber so that the sample was level with the cap (no bulging) and the rubber washer was in proper seating position.

The foil sample assembly was removed from the chamber and weighed immediately to the nearest 0.01 gram for an initial dry weight, W1. The assembly was then returned to the chamber for at least 18 hours, the exposure time T1 in hours, after which it was removed and weighed immediately to the nearest 0.01 g for a final dry weight, W2. The MVTR in grams of water vapor transmitted per square meter of sample area per 24 hours can then be calculated using the following formula.

$$\text{Upright (Dry) MVTR} = (W1 - W2) \times (4.74 \times 10^4)/T1$$

Moisture Vapor Transmission Rate—Inverted (Wet) MVTR Method

The inverted MVTR was measured using the following test procedure. After obtaining the final "dry" weight, W2, as described for the upright MVTR procedures, the assembly was returned to the chamber for a least 18 additional hours of exposure time, T2, with the jars inverted so that the tap water was in direct contact with the test sample. The sample was then removed from the chamber and weighed to the nearest 0.01 gram for a final wet weight, W3. The inverted wet MVTR in grams of water vapor transmitted per square meter of sample area per 24 hours can then be calculated using the following formula.

$$\text{Inverted (Wet) MVTR} = (W2 - W3) \times (4.74 \times 10^4)/T2$$

Antimicrobial Efficacy Test Method

The procedures summarized below as 1) Bactericidal Assay and 2) Bacteriostatic Assay were used for the microbiological assessment of subsequent examples of antiseptic gel compositions. The Antimicrobial Efficacy Test includes either the Bactericidal Assay, the Bacteriostatic Assay, or both.

The following materials were used in the microbiological test procedure: Tryptic Soy Broth (TSB), available from Becton, Dickinson and Company (BD) of Franklin Lakes, N.J. (USA), under the tradename BACTO; D/E Neutralizing Broth, available from BD under the tradename DIFCO; FBS (Fetal Bovine Serum), Certified, available from Gibco by Live Technologies; Phosphate Buffer Saline (PBS) solution; BD Falcon 50 mL Polypropylene Conical Test Tubes, available from BD; Mini Flip-Top Vial with Butterfields Buffer, available from 3M Company of St. Paul, Minn. (USA); and PETRIFILM Aerobic Count Plate (AC) 6400/6406/6442, available from 3M Company of St. Paul, Minn. (USA).

Cultures of *Staphylococcus aureus* (ATCC No. 6538), *Escherichia coli* (ATCC No. 25922), and *Pseudomonas aeruginosa* (ATCC No. 9027) in 20 mL of TSB were obtained fresh, overnight (18-24 hours).

1. Antimicrobial Efficacy—Bactericidal Assay Procedure:

Antiseptic gel solutions were prepared by diluting the concentrated gel (solids 20%-27%) in 1:1 ratio with the appropriate solvent (isooctane or HMDS) to a final volume of 8 mL. The test solutions were prewarmed to 32° C. in a heating plate while being stirred. 1 mL of serum and 1 mL of appropriate bacterial test culture was pipetted into the 8 mL of test sample. The samples were vortex mixed for 30 seconds, then incubated at 32° C. for 10 min. Duplicates of 1 mL sample aliquots were removed and mixed into 9 mL of D/E neutralizing broth in 50 mL conical tubes that were previously filled. The samples were vortex mixed for 30 seconds at high speed, then placed into an ice bath. The neutralized samples were diluted with a 1:10 serial dilution using the 9 mL Butterfields Buffer test tubes. The dilutions were completed by adding 1 mL of the sample fluid into 9 mL of Butterfields Buffer for the 1:10 dilution. Next, 1 mL from the 1:10 dilution tube was pipetted into 9 mL of Butterfields Buffer to make the 1:100 dilution. Then, pipetted 1 mL from the 1:100 dilution tube into 9 mL of Butterfields Buffer for a 1:1000 dilution. Finally, pipetted 1 mL from the 1:1000 dilution tube into 9 mL of Butterfields Buffer for a 1:10000 dilution. The samples were plated by vortexing the diluted samples and pipetting 1 mL aliquots from these tubes onto the PETRIFILM Aerobic Count Plates. The plating process was completed to negative five (−5) dilutions, which are also notated as 1:1, 1:10, 1:100, 1:1000, 1:10000. The samples were placed in a 37° incubator for 24 hours, then, read with a PETRIFILM PLATE READER (available from 3M Company of St. Paul, Minn.) and the number of colonies recorded and reported as Log (10) Recovery. Log(10) Reduction was also calculated and reported. Log Reduction is calculated by subtracting the log recovered from the control, which in this case is an 8 mL PBS solution inoculated with 1 mL of the same bacterial suspension and 1 mL of FBS.

2. Antimicrobial Efficacy—Bacteriostatic Assay Procedure:

Antiseptic gel solutions were prepared by diluting the concentrated gel (solids 20%-27%) in 1:1 ratio with the appropriate solvent (isooctane or HMDS) to a final volume of 8 mL. The test solutions were prewarmed to 32° C. in a heating plate while being stirred. 1 mL of serum and 1 mL of appropriate bacterial test culture was pipetted into the 8 mL of test sample. 1 mL aliquots were pipetted from this test mixture and placed into duplicate flasks containing 100 mL of TSB without neutralizers and mixed well. These samples were incubated at 37° C. for 48 hours. The samples were then diluted with a 1:10 serial dilution using the Butterfields Buffer test tubes. The dilutions were completed by adding 1 mL of the sample fluid into 9 mL of Butterfields Buffer for the 1:10 dilution. Next, 1 mL from the 1:10 dilution tube was pipetted into 9 mL of Butterfields Buffer to make the 1:100 dilution. Then, pipetted 1 mL from the 1:100 dilution tube into 9 mL of Butterfields Buffer for a 1:1000 dilution. Finally, pipetted 1 mL from the 1:1000 dilution tube into 9 mL of Butterfields Buffer for a 1:10000 dilution. The samples were plated by vortexing the diluted samples and pipetting 1 mL aliquots from these tubes onto the PETRIFILM Aerobic Count Plates. The plating process was completed to negative five (−5) dilutions, which are also notated as 1:1, 1:10, 1:100, 1:1000, 1:10000. The samples were placed in a 37° incubator for 24 hours, then, read with a PETRIFILM PLATE READER (available from 3M Company of St. Paul, Minn.) and the number of colonies recorded and reported as Log(10) Reduction. Log Reduction is calculated by subtracting the log recovered from the input control, which is an 8 mL PBS solution inoculated with 1 mL of the same bacterial suspension and 1 mL of FBS.

Testing of Exemplary Compositions

The materials used in the following examples are summarized in Table 1.

TABLE 1

Summary of materials.

| Material | Description | Source |
|---|---|---|
| Silicone Polyoxamide (SPOx) | Poly(diorganosiloxane)-polyoxamide copolymer made from a diamine of 25,000 molecular weight as per "Preparatory Example 1" of U.S. Pat. No. 7,947,376. | — |
| HMDS | Hexamethyldisiloxane | Wacker Chemical, Chicago, IL |
| ISO | Isooctane | Ineos Group AG, Rolle, Switzerland |
| MQ | Silicate tackifying resin | Wacker Chemical, Chicago, IL |
| g-PEI | Crosslinked, Guanidinylated polyethylenimine | Preparatory Example 1 Below |
| BZT | Benzylthonium Chloride, 97% | Alfa Aesar, Ward Hill, MA |
| PDMS | Monocarboxydecyl terminated polydimethylsiloxane fluid, silicone surfactant | Gelest, Inc., Morrisville, PA |
| R 8200 | HMDS treated fumed silica | Evonik Corp., Piscataway, NJ |
| Kaolin | KA105, china clay powder | Spectrum Chemical MFG. Corp., New Brunswick, NJ |
| Sensiva SC10 | 1,2-octanediol, 3-[(2-ethylhexyl)oxy]-1,2-propanediol | Schülke & Mayr GmbH, Germany |
| NSNF | Non-silicone non-fluorinated release film | Described in US2009/0000727 |

All formulation components are reported in percent weight/weight (% wt/wt) unless otherwise noted.

Preparatory Example 1

Synthesis Steps for Making Cross-Linked Guanylated Polyethylenimine (g-PEI)

A 12 L 3 neck split top resin flask was charged with 1250 g of aqueous polyethylenimine solution (mw 75,000, 32.6% solids, BASF Lupasol PS) followed by 1279 g of DI water. The flask was equipped with an overhead stirrer and 291.6 g O-methyl isourea hemisulfate was added and the mixture was stirred overnight. An aliquot was taken from the viscous solution and checked by 1H NMR (CD3OD—deuterated methanol) to monitor the disappearance of the O-methyl isourea hemisulfate. The solution was transferred to a polypropylene bottle rinsing with a little water followed by measuring percent solids (21.1% by Ohaus).

The solution was then treated with 3401 g of heptanes and stirred for 5 minutes. 1,4-Butanediol diglycidyl ether (BUDGE, 91.5 g) was and the solution was stirred over night (16 hours). Stirring ceased and the heptane and DI water was removed from solution with a vacuum filter stick (coarse porosity). The resulting gel was washed with IPA to draw off remaining heptane. 2176 g of isopropyl alcohol was added to the flask. The composition was stirred vigorously for 10 minutes and then filtered using the filter stick. This procedure was repeated three more times. The resulting white solid was then filtered using a nutsche filter and dried in a vacuum oven at 100° C.

The dried beads are then jet milled using a 3000 rpm Model 100/20 jet miller. The dried beads are placed in a hopper then feed into an air stream tube. The air stream carries the beads to a splitter where the beads are pushed through two smaller tubes and eventually forced through a cone shaped nozzles (jets). The jets are positioned so the beads colloid into each other, the impact reduces the particle size. After the collision the air stream carries the bead particles to a classifier. The classifier, depending on its rotational speed will allow small particles to be collected while larger particles are returned to the air stream to be jet milled again. Generally the higher classifier speed results in finer particle size.

Gel Composition Sample Preparation

The following steps were used in creating all gel compositions in the Examples below. PDMS was pipetted using a 2 mL pipette into a 125 mL clear glass jar. HMDS was added to the solution jar which was then capped to prevent evaporation. MQ, g-PEI, Sensiva SC10, and BZT were subsequently added in that order to the reaction jar. During addition of the g-PEI, the material was crushed in a weighing dish with a spatula to remove clumps. The mixture solution was placed in an ice bath (4° C.), where the solution was dispersed using a Polytron PT 2500E (available from Kinematica, Inc., Bohemia N.Y.) for 20 minutes at 18.5× 1000 RMP. After dispersion, a stir bar was added to the solution jar which was then placed in a hot water bath (66° C.) on a heating and stirring mantle. SPOx was then added immediately and the jar capped. The solution was mixed for 2 hours. After two hours, the jar was sealed with SCOTCH Thread Sealant Tape (available from 3M Company, St. Paul, Minn.) and placed on a roller.

Examples 1-3

Examples 1-3 were formulated to examine both the Upright and Inverted MVTR of a dried film. The weight percent of components used in the formulations for the gel compositions of Example 1-3 are shown in Table 2A below. To prepare film samples, the gel composition was applied, using a syringe, to a polyethylene film clamped down to a flat glass panel. A Gardco Microm II adjustable micrometer film applicator, set to a specific (e.g., 50 mil) thickness, was pulled across the gel to form a thin layer. The films were dried in a hood for 20 minutes and then die cut to produce circular, 3.8 cm diameter samples. Example 4 is a NEXCARE TEGADERM Waterproof Transparent Dressing, available from 3M Company, St. Paul, Minn.

All MVTR data shown use this test condition and reported with the unit of $g/m^2/24$ hours. The coating thickness for each of the samples was 50 mils. The samples were tested and the results are shown in Table 2B.

TABLE 2A

Composition of Examples 1-3.

| Components | Ex. 1 Wet (Gel) | Ex. 1 Dry (Film) | Ex. 2 Wet (Gel) | Ex. 2 Dry (Film) | Ex. 3 Wet (Gel) | Ex. 3 Dry (Film) |
|---|---|---|---|---|---|---|
| SPOx | 17.61 | 70.45 | 15.00 | 60.01 | 12.39 | 49.58 |
| g-PEI | 0.75 | 2.99 | 2.99 | 11.95 | 5.23 | 20.90 |
| PDMS | 0.37 | 1.49 | 1.49 | 5.97 | 2.61 | 10.45 |
| BZT | 0.20 | 0.80 | 0.20 | 0.80 | 0.20 | 0.80 |
| Sensiva SC10 | 1.00 | 4.00 | 1.00 | 4.00 | 1.00 | 4.00 |
| MQ | 5.07 | 20.27 | 4.32 | 17.27 | 3.57 | 14.27 |
| HMDS | 75.00 | 0.0 | 75 | 0.0 | 75 | 0.0 |
| Total Wt. % | 100.0 | 100.0 | 100.0 | 100.0 | 100.0 | 100.0 |
| % Solids | 25 | 100 | 25 | 100 | 25 | 100 |

Multiple samples of the Examples below were measured for Upright (Dry) and Inverted (Wet) MVTR according to the test methods described above. The average results are reported below, followed by the standard deviation (+/−) of the multiple samples.

TABLE 2B

MVTR of Examples 1-4

| | Example | | |
|---|---|---|---|
| | 1 | 2 | 3 |
| Upright MVTR (±95% confidence) | 627 (±54) | 728 (±72) | 783 (±57) |
| Inverted MVTR ((±95% confidence) | 648 (±115) | 956 (±124) | 1020 (±163) |

Examples 4-7

A variety of different coating weights of the formulation of Example 2 were tested to examine the impact of coating weight and film thickness on moisture transmission. The coating weight for each of the sample, as well as the resulting film thickness is Example 4-7 are shown in Table 3 below. Multiple samples of the Examples below were measured for Upright (Dry) and Inverted (Wet) MVTR according to the test methods described above. The average results are reported below, followed by the standard deviation (+/−) of the multiple samples.

TABLE 3

MVTR of Examples 4-7

| | Example | | | |
|---|---|---|---|---|
| | 4 | 5 | 6 | 7 |
| Coating thickness (mil) | 25 | 50 | 100 | 200 |
| Film Thickness (mil) | 3 | 6 | 13 | 26 |
| Upright MVTR (±95% confidence) | 1229 (±132) | 728 (±72) | 353 (±56) | 220 (±45) |
| Inverted MVTR (±95% confidence) | 1446 (±123) | 956 (±124) | 569 (±196) | 231 (±69) |

Examples 8-13

Examples 8-13 was conducted to evaluate the antimicrobial efficacy of various gel formulations with BZT. The weight percent of components used in the formulations for the gel composition samples of Example 8-13 are shown in Table 4 below. Example 13 is the control Phosphate Buffer Saline (PBS) solution.

TABLE 4

Antimicrobial efficacy of Examples 8-13

| Components | Ex. 8 | Ex. 9 | Ex. 10 | Ex. 11 | Ex. 12 | Ex. 13 |
|---|---|---|---|---|---|---|
| SPOx | 15.35 | 15.35 | 15.29 | 15.29 | 16.07 | 0.0 |
| g-PEI | 4.42 | 4.42 | 4.41 | 4.41 | 2.43 | 0.0 |
| PDMS | 2.21 | 2.21 | 2.20 | 2.20 | 1.22 | 0.0 |
| BZT | 0.10 | 0.10 | 0.20 | 0.20 | 0.2 | 0.0 |
| Sensiva SC10 | 1.0 | 1.0 | 1.0 | 1.0 | 1 | 0.0 |
| MQ | 4.42 | 4.42 | 4.40 | 4.40 | 4.4 | 0.0 |
| Kaolin | 0.0 | 0.0 | 0.0 | 0.0 | 0.54 | 0.0 |
| R8200 | 0.0 | 0.0 | 0.0 | 0.0 | 1.65 | 0.0 |

TABLE 4-continued

Antimicrobial efficacy of Examples 8-13

| Components | Ex. 8 | Ex. 9 | Ex. 10 | Ex. 11 | Ex. 12 | Ex. 13 |
|---|---|---|---|---|---|---|
| ISO | 0.0 | 0.0 | 0.0 | 0.0 | 72.5 | 0.0 |
| HMDS | 75.50 | 75.5 | 75.5 | 75.5 | 0.0 | 0.0 |
| PBS | 0 | 0 | 0 | 0 | 0 | 100.0 |
| Total Wt. % | 100.0 | 100.0 | 100.0 | 100.0 | 100.0 | 100.0 |
| Dilution | 1:1 | 1:3 | 1:1 | 1:3 | 1:1 | |
| Ave. Log Recovery at 10 minutes (*E. Coli*) | <1 | <1 | <1 | <1 | <1 | 6.36 |
| Std Dev (at 10 min) (*E. Coli*) | 0 | 0 | 0 | 0 | 0 | 0.15 |
| Ave. Log Recovery at 10 minutes (*S. aureus*) | 1.57 | 1.78 | <1 | <1 | 1.15 | 6.57 |
| Std Dev (at 10 min) (*S. aureus*) | 0.57 | 0.3 | 0 | 0 | 0.15 | 0.04 |
| Ave. Log Recovery at 10 minutes (*P. aeurginosa*) | 1.57 | 3.62 | <1 | 3.31 | <1 | 6.73 |
| Std Dev (at 0 min) (*P. aeruginosa*) | 0.27 | 0.13 | 0 | 0.8 | 0 | 0.01 |

Examples 14-18

Examples 14-18 were formulated to examine both the tensile and elongation of dried film generally in accord with ASTM D882-12. The weight percent of components present in the dried films of Example 14-18 are shown in Table 5 below. Gel compositions of the samples were coated on a 1 mil thick NSNF at 50 mils wet (the Gardco Microm II applicator set at 51 mils) and allowed to dry overnight at room temperature and pressure. The dried films were razor cut into 1×2 inches strips and tabs on the strips ends were made using masking tape. For each sample, the tabs were secured in the grips of a constant rate tensile tester (Zwick/Roell Z005). Gauge length was set at 1" and cross-head speed was set at 10"/min. The grips were drawn apart until the sample ruptured or broke. Each sample was run in triplicate.

TABLE 5

Mechanical Properties of Examples 14-18

| Components | Ex. 14 | Ex. 15 | Ex. 16 | Ex. 17 | Ex. 18 |
|---|---|---|---|---|---|
| SPOx | 67.0 | 65.5 | 59.1 | 59.1 | 59.1 |
| g-PEI | 8.3 | 17.0 | 8 | 8 | 8 |
| BZT | 0.0 | 0.0 | 0.70 | 0.70 | 0.70 |
| PDMS | 0.0 | 0.0 | 4.0 | 4.0 | 4.0 |
| MQ | 13.0 | 12.5 | 0.0 | 5.5 | 16.5 |
| Kaolin | 0.0 | 0.0 | 2.5 | 2.5 | 2.5 |
| R8200 | 12.3 | 5.0 | 22.0 | 16.5 | 5.5 |
| Sensiva SC-10 | 0.0 | 0.0 | 3.6 | 3.6 | 3.6 |
| Total Wt. % | 100.0 | 100.0 | 100.0 | 100.0 | 100.0 |
| Elongation at break (%) | 836 | 631 | 87 | 329 | 979 |
| Ultimate Tensile Strength (MPa) | 0.52 | 0.68 | 0.71 | 0.65 | 0.68 |
| Brookfield Viscosity (cps) | 294,700 | 180,100 | 113,800 | 92,800 | 71,200 |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:
1. A film forming gel composition comprising:
   10-30 wt. % of a silicone containing, film forming polymer based on the total weight of the gel composition, wherein the silicone containing, film forming polymer comprises a polydiorganosiloxane polyoxamide;
   3-20 wt. % of a tackifier based on the total weight of the gel composition, the tackifier comprising a silicate tackifying resin;
   0.5-20 wt % of a plurality of coagulant particles based on the total weight of the gel composition, the plurality of coagulant particles comprises a crosslinked guanidinyl-containing polymer having primary or secondary amino groups;
   and 60-80 wt/ % of a volatile solvent based on the total weight of the film forming gel composition, and wherein a film cast from the film forming gel composition is self-supporting on a biological substrate and can be peeled off the substrate without substantially compromising the integrity of the film such that at least a portion of the film is removable in a single continuous layer.

2. The composition of claim 1, further comprising 0.1-15 wt. % silicone surfactant, based on the total weight of the gel composition.

3. The composition of claim 1, wherein the guanidinyl-containing polymer is an aminopolymer functionalized with one or more guanidinyl groups.

4. The composition of claim 3, wherein the guanidinyl-containing polymer is guanidinylated polyethyleneimine.

5. The composition of claim 1, wherein the coagulant comprises at least 1.5 wt. % and no greater than 10 wt. % of the gel composition based on the total weight of the gel composition.

6. The composition of claim 1, wherein the tackifier comprises an MQ silicate tackifying resin.

7. The composition of claim 1 and further comprising an antiseptic agent, wherein the antiseptic comprises at least one of octenidine, chlorhexidine salt, alexidine salt, polyhexamethylene biguanide salt, benzalkonium salt, cetyl pyridinium salt, cetrimonium salt, or benzethonium salt, and combinations thereof.

8. The composition of claim 7, wherein the antiseptic is present at a concentration of at least 0.1 wt. % and no greater than 1.0 wt. %, based on the total weight of the gel composition.

9. The composition of any claim 8, wherein the active kill of a dried film cast from the gel composition is at least 3 log reduction of a target microorganism according to the Antimicrobial Efficacy Test Method, and wherein the target microorganism is one or more of *Staphylococcus aureus, Escherichia coli*, and *Pseudomonas aeruginosa*.

10. The composition of claim 7, wherein the gel composition includes an effective amount of an antiseptic surfactant, the antiseptic surfactant comprising a straight chain 1,2-alkanediols having a chain length in the range of 5 to 10 carbon atoms.

11. The composition of claim 1, wherein the volatile solvent is selected from the group consisting of volatile linear and cyclic siloxanes, volatile polydimethylsiloxanes, isooctane, octane, and combinations thereof.

12. The composition of claim 1, wherein a film cast from the gel composition exhibits an elongation of at least 100%, and an ultimate tensile strength of at least 0.3 MPa after drying on a biological substrate.

13. The composition of claim 12, wherein the film exhibits an upright MVTR of at least 300 $g/m^2/24$ hours, a Skin Adhesion of at least 50 g/inch and no greater than 900 g/inch.

* * * * *